US010167451B2

(12) United States Patent
Lee et al.

(10) Patent No.: US 10,167,451 B2
(45) Date of Patent: Jan. 1, 2019

(54) COMBINATIONAL USE OF MECHANICAL MANIPULATION AND PROGRAMIN DERIVATIVES TO INCREASE OCT4, SOX2, OR NANOG EXPRESSION IN FIBROBLASTS

(71) Applicant: The Chinese University of Hong Kong, Shatin, New Territories (CN)

(72) Inventors: Kenneth Ka Ho Lee, Hong Kong (CN); Tommy Lok Man Lo, Hong Kong (CN); Hoi Hung Cheung, Kowloon (CN); Wai Yee Chan, Hong Kong (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 125 days.

(21) Appl. No.: 14/579,784

(22) Filed: Dec. 22, 2014

(65) Prior Publication Data

US 2016/0177271 A1 Jun. 23, 2016

(51) Int. Cl.
*C12N 5/074* (2010.01)

(52) U.S. Cl.
CPC ........ *C12N 5/0696* (2013.01); *C12N 2500/40* (2013.01); *C12N 2501/999* (2013.01); *C12N 2506/1307* (2013.01); *C12N 2506/1392* (2013.01); *C12N 2527/00* (2013.01)

(58) Field of Classification Search
CPC .............. C12N 5/0696; C12N 2500/40; C12N 2501/999; C12N 2506/025; C12N 2506/09; C12N 2506/1307; C12N 2506/1392; C12N 2527/00
See application file for complete search history.

(56) References Cited

U.S. PATENT DOCUMENTS

| | | | |
|---|---|---|---|
| 5,265,075 | A | 11/1993 | Bergeron et al. |
| 7,176,312 | B2 | 2/2007 | Ding et al. |
| 7,273,864 | B2 | 9/2007 | Wu et al. |
| 7,442,548 | B2 | 10/2008 | Thomson et al. |
| 7,541,186 | B2 | 6/2009 | Reh et al. |
| 7,592,177 | B2 | 9/2009 | Chen et al. |
| 7,757,762 | B2 | 7/2010 | O'Malley |
| 7,781,214 | B2 | 8/2010 | Smith et al. |
| 8,187,878 | B2 | 5/2012 | Dalton et al. |

OTHER PUBLICATIONS

Ebrahimi B. "Chemical-only reprogramming to pluripotency." Front. Biol. (2016) 11: 75*
Wei et al. "Small molecule compound induces chromatin de-condensation and facilities induced pluripotent stem cell generation." J Mol Cell Biol. Oct. 2014;6(5):409-20.*
Gaspar-Maia et al. "Open chromatin in pluripotency and reprogramming." Nat Rev Mol Cell Biol. Jan. 2011;12(1):36-47.*
Hou et al. "Pluripotent stem cells induced from mouse somatic cells by small-molecular compounds."Science. Aug. 9, 2013;341(6146):651-4.*
Wei et al. "Supplementary Data. Small molecule compound induces chromatin de-condensation and facilitates induced pluripotent stem cell generation."J Mol Cell Biol. Oct. 2014;6(5):409-20.*
De Los Angeles et al. "Hallmarks of pluripotency."Nature. Sep. 24, 2015;525(7570):469-78.*
Hou et al. "Supplementary Data. Pluripotent stem cells induced from mouse somatic cells by small-molecule compounds."Science. Aug. 9, 2013;341(6146):651-4.*
Andrews et al., "Induction of Class I Major Histocompatibility Complex Antigens in Human Teratocarcinoma Cells by Interferon without Induction of Differentiation, Growth Inhibition, or Resistance to Viral Infection", *Cancer Research*, 47:740-746 (1987).
Anastasia et al., "Reversine-treated fibroblasts acquire myogenic competence in vitro and in regenerating skeletal muscle", *Cell Death and Differentiation*, 13(12): 2042-2051 (2007).
Ausubel et al., eds., "Chapter 4: Preparation and Analysis of RNA", Current Protocols in Molecular Biology, pp. 4.0.1-4.2.9 (1994).
Beaucage et al., Deoxynucleoside phosphoramidites—A new class of key intermediates for deoxypolynucleotide synthesis:, *Tetrahedron Lett.*, 22:1859-1862 (1981).
Berge et al., "Pharmaceutical Salts", *Journal of Pharmaceutical Sciences*, 66:1-19 (1977).
Chen et al., "Differentiation of Lineage-Committed Cells by a Small Molecule", *J. Am. Chem. Soc.*, 126: 410-411 ( 2004).
Ding et al., "A Combinatorial Scaffold Approach toward Kinase-Directed Heterocycle Libraries", *J. Am. Chem. Soc.*, 124:1594 (2002).
Discher et al., "Inorganic Pharmaceutical Chemistry", *Remington: The Science and Practice of Pharmacy*, Mack Publishing Company, Philadelphia, PA, 19th ed., p. 315-339 (1995).
Fania et al., "Proteomic signature of reversine-treated murine fibroblasts by 2-D difference gel electrophoresis and MS: Possible associations with cell signaling networks", *Electrophoresis*, 30(12): 2193-2206 (2009).
Freshney et al., "Chapter 2: Biology of the Cultured Cell", *Culture of Animal Cells*, pp. 9-16 (3rd ed. 1994).
Good et al., "hydrogen Ion Buffers for Biological Research", *Biochemistry*, 5:467-477 (1966).
Hockemeyer et al., "A Drug-Inducible System for Direct Reprogramming of Human Somatic Cells to Pluripotency", *Cell Stem Cell*, 3:346-53 (2008).
Huangfu et al., "Induction of pluripotent stem cells by defined factors is greatly improved by small-molecule compounds", Nature Biotechnology, 26:795-797, abstract only.
Humason, "Chapter 23: Special Procedures II", Animal Tissue Techniques, 4.sup.th ed., W.H. Freeman and Company, pp. 461-492 (1979).
Kriegler, "PCT-Based Expression", *Gene Transfer and Expression: A Laboratory Manual*, pp. 165-176 (1990).
Liu et al., "Cryopreservation of Human Pluripotent Stem Cells in Defined Medium", *Current Protocols in Stem Cell Biology*, 1C.17. 1-16.13, New York: Wiley (2014).

(Continued)

*Primary Examiner* — Titilayo Moloye
(74) *Attorney, Agent, or Firm* — Kilpatrick Townsend & Stockton LLP

(57) ABSTRACT

The present invention provides methods and compositions for inducing pluripotency in differentiated mammalian cells. In particular, the methods include mechanically aggregating the cells into discrete masses or embryoid-like bodies and treated them with a small molecule compound. Provided herein are the compositions of the compounds which are derived from programin (e.g., reversine).

10 Claims, 10 Drawing Sheets

(56) References Cited

OTHER PUBLICATIONS

Lowry et al., "Generation of human induced pluripotent stem cells from dermal fibroblasts", *Proc Natl Acad Sci U S A.*, 105(8):2883-2888 (2008).

Ludwig et al., "Derivation of human embryonic stem cells in defined conditions", *Nat. Biotechnology*, 24(2): 185-187 (2006).

Ludwig et al., "Feeder-independent culture of human embryonic stem cells", *Nature Methods*, 3:637-646 (2006).

Maherali et al., "Directly Reprogrammed Fibroblasts Show Global Epigenetic Remodeling and Widespread Tissue Contribution", *Cell Stem Cell*, 1:55-70 (2007).

Mandal et al., "Gene expression profile associated with the reversine-mediated transdifferentiation of NIH-3T3 fibroblast cells into osteoblasts", *Biochip Journal*, 7(3): 278-287 (2013).

Marson et al., "Wnt Signaling promotes reprograming of somatic cells to pluripotency", *Cell Stem Cell*, 3(2):132-135 (2008).

Meissner et al., "Direct reprogramming of genetically unmodified fibroblasts into pluripotent stem cells", *Nature Biotechnol.*, 25:1177-1181 (2007).

Nakagawa et al., "Generation of induced pluripotent stem cells without Myc from mouse and human fibroblasts", *Nature Biotechnol.*, 26:101-106 (2008).

Needham-Vandevanter et al., "Characterization of an adduct between CC-1065 and a defined oligodeoxynucleotide duplex", *Nucleic Acids Research*, 12(15):6159-6168 (1984).

Nichols et al., "Formation of Pluripotent Stem Cells in the Mammalian Embryo Depends on the POU Transcription Factor Oct4", *Cell*, 95:379-391 (1998).

Okamoto et al., "A novel octamer binding transcription factor is differentially expressed in mouse embryonic cells", *Cell*, 60(3):461-472 (1990), abstract only.

Okita et al., "Generation of germline-competent induced pluripotent stem cells", *Nature*, 448: 313-317 (2007).

Park et al., "Generation of Multipotent CD34+CD45+ Hematopoletic Progenitors from Human Induced Pluripotent Stem Cells", *Human Embryonic and Induced Pluripotent Stem Cells: Lineage-Specific Differentiation Protocols*, Springer Protocols Handbook: , pp. 337-350 (2012).

Pearson et al., "High-performance anion-exchange chromatography of oligonucleotides", *Journal of Chromatography*, 255: 137-149 (1983).

Ricciardelli et al., "Development and Characterization of Primary Cultures of Smooth Muscle Cells from the Fibromuscular Stroma of the Guinea Pig Prostate", *In Vitro Cell Dev. Biol.*, 25(11):1016-1024 (1989).

Rodolfa et al., "A Transcriptional Logic for Nuclear Reprogramming", *Cell*, 126:652-655 (2006).

Sambrook et al., *Molecular Cloning: A Laboratory Manual*, Table of Contents, 21 pages. (3rd ed. 2001).

Schlaeger et al., ed., Culture and Maintenance of Undifferentiated Embryonic Stem cells:, *Current Protocols in Stem Cell Biology*, 1C.01--1C.02, New York: Wiley (2014).

Park et al., "Reprogramming of human somatic cells to pluripotency with defined factors", *Nature*, 451(7175):141-146 (2008).

Shan et al., "Induction of groth arrest and polycomb gene expression by reversine allows C2C12 cells to be repgrogrammed to various differentiated cell types", *Proteomics*, 7(23): 4303-4316 (2007).

Song et al., "Generation, Expansion, and Differentiation of Human Induced Pluripotent Stem Cells (hiPSCs) Derived from the Umbilical Cords of Newborns", *Current Protocols in Stem Cell Biology*, 1C.16.1-16.13, New York: Wiley (2014).

Shi et al., "Induction of Pluripotent Stem Cells from Mouse Embryonic Fibroblast by Oct4 and Klf4 with Small-Molecule Compounds", *Cell-Stem Cell*, 3:568-574 (2008).

Shi et al., "A combined chemical and genetic approach for the generation of induced pluripotent stem cells", *Cell Stem Cell*, 2:525-528 (2008).

Takahashi et al., "Induction of Pluripotent Stem Cells from Mouse Embryonic and Adult Fibroblast Cultures by Defined Factors", *Cell*, 126(4):663-676 (2006).

Takahashi et al., "Induction of Pluripotent Stem Cells from Adult Human Fibroblast by Defined Factors", *Cells*, 131:861-872 (2007).

Wernig et al., "In vitro reprogramming of Fibroblast into a pluripotent ES-cell-like state", *Nature*, 318-324 (2007).

Wernig et al., "c-MYC is Dispensable for Direct Reprogramming of Mouse Fibroblast", *Cell Stem Cell.*, 2:10-12 (2008).

Yu et al., "Induced Pluripotent Stem Cell Lines Derived from Human Somatic Cells", *Science*, 318:1917-1920 (2007).

\* cited by examiner

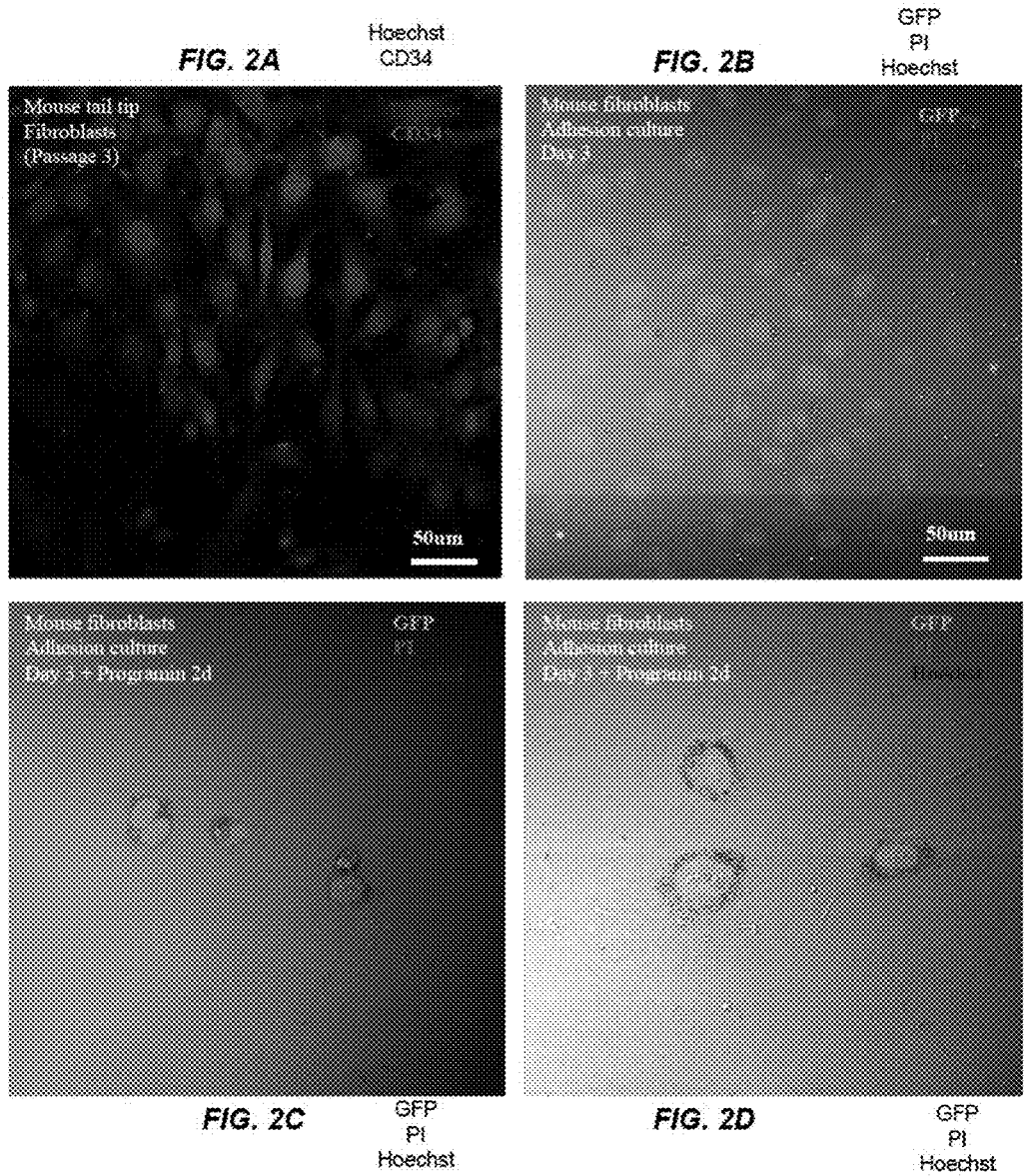

Figure 2. (A) Fibroblasts extracted from the tail of Oct4-EGFP transgenic mice. The cells were sorted by flow cytometry for only those expressing CD34 surface markers. (B) Representative appearance of CD34+ fibroblasts grown on adhesive culture dishes for 3 days (C and D). Representative appearance of CD34+ fibroblasts grown on adhesive culture dishes and treated with 5μM programin for 3 days. A majority of fibroblasts had died and no Oct4-EGFP expression was detected.

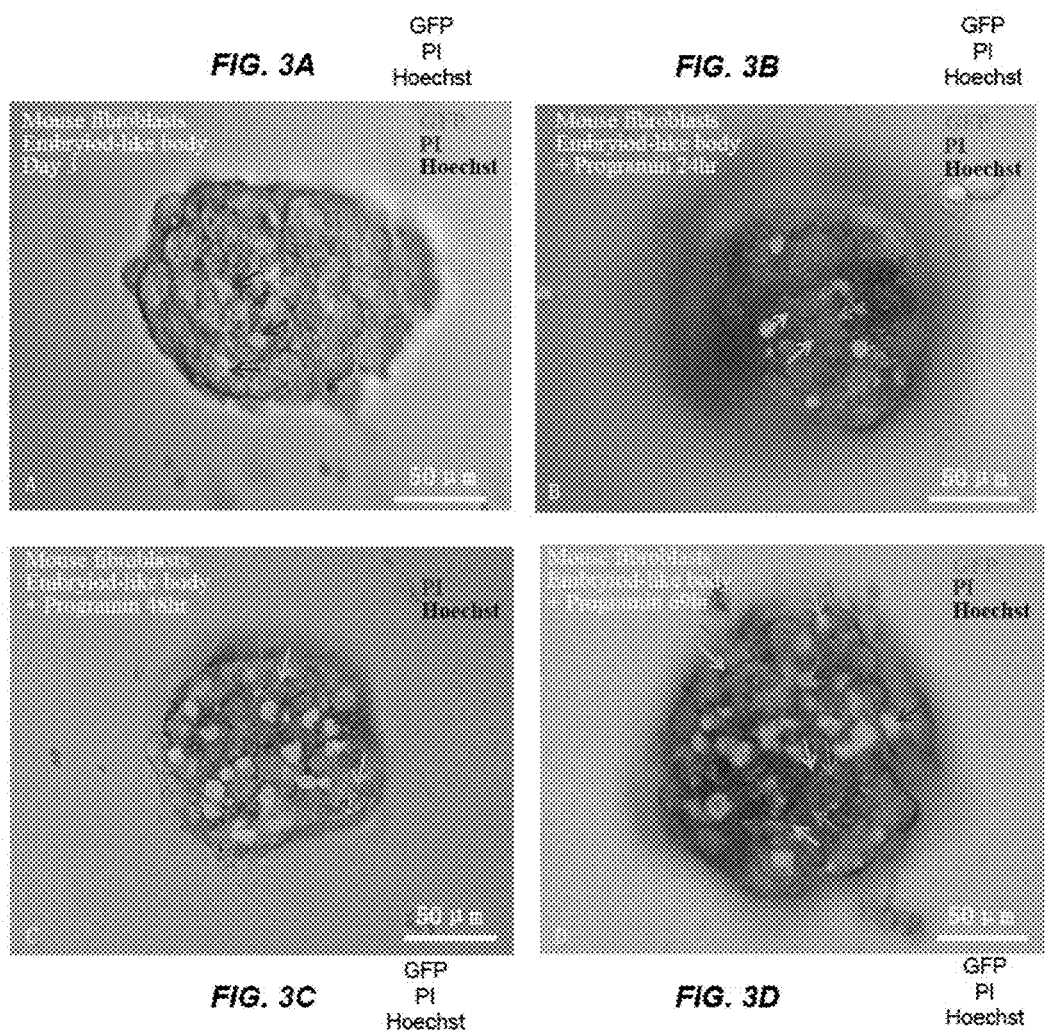

Fig 3. (A) showing CD34+ fibroblasts were mechanically pipetted and maintained on hydrophobic non-adhesive culture plates so that the cells aggregate to form embryoid-like bodies. These embryoid-like bodies were stained with PI dye to reveal the presence of dead cells (red arrows) and Hoechst dye for the presence of live cells (blue arrows). Under the confocal microscope, Oct4-EGFP expression (green arrows) was undetectable in the live cells of all non-Programin-treated embryoid-like bodies. (C, D, E) Representative appearance of the embryoid-like cell bodies treated with 5μM of Programin for 1-3 days. Programin could induce Oct4-EGFP expression (green arrows) in the CD34+ fibroblasts 24 - 69 hours after Programin treatment.

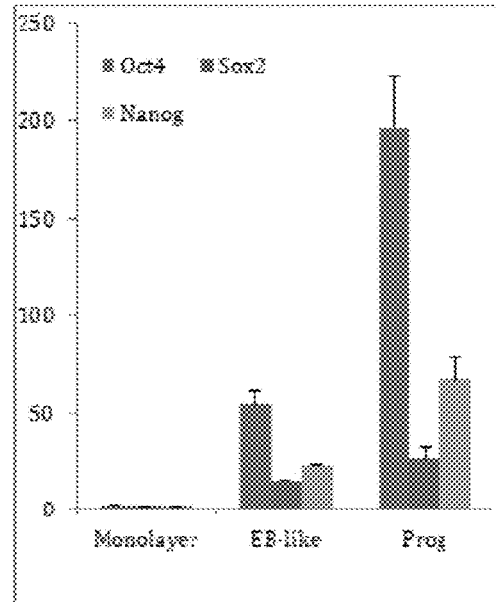

Fig 4. qPCR analysis showing CD34+ mouse fibroblasts grown as a monolayer on adhesive culture dishes do not express *Oct4*, *Sox2* and *Nanog*. In contrast, when the fibroblasts are mechanically manipulated and maintained on hydrophobic culture plates to form embryoid-like (EB-like) cell bodies - they are induced to express very low levels of the three pluripotent genes. Furthermore, treatment of these embryoid-like cell bodies with 5μm Progranulin (Prog) for 3 days significantly up-regulated *Oct4*, *Sox2* and *Nanog* expression.
Y-axis: Fold changes in *Oct4*, *Sox2* and *Nanog* expression relative to the monolayer control. All samples have been normalized against GAPDH.

NB: an embryoid-like body = an aggregate of CD34+ mouse fibroblasts.

*FIG. 4*

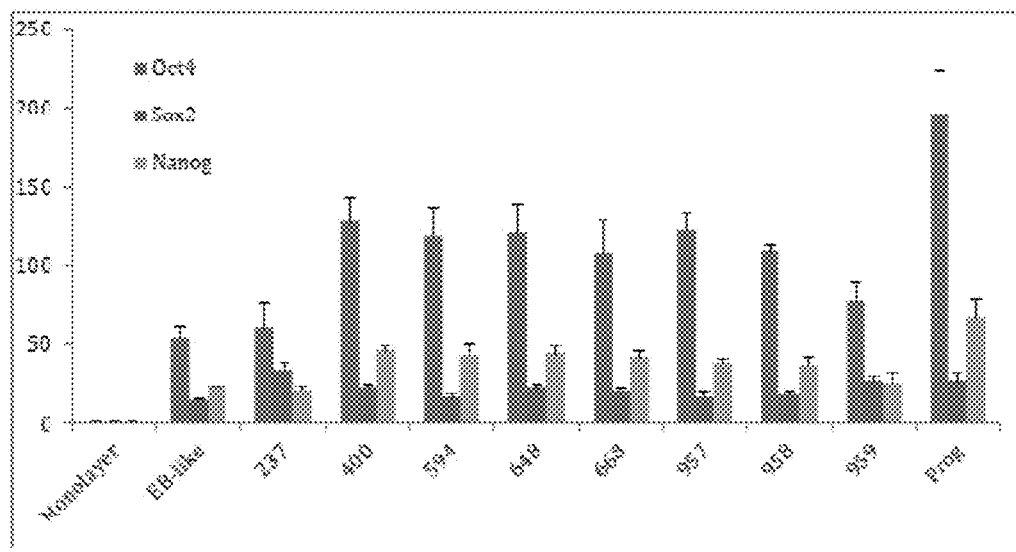

Fig 5. RT-qPCR analysis showing the efficacy of our Programin derivatives to activate *Oct4*, *Sox2* and *Nanog* expression. Programin derivatives 237, 400, 594, 648, 668, 957, 958 and 959 could significantly activate and elevate *Oct4*, *Sox2* and *Nanog* expression in the embryoid-like (EB-like) cell bodies by many folds. However, the fold increase in expression of these pluripotent genes was not as high as compare with the lead molecule, Programin (Prog).
Y-axis: Fold changes in *Oct4*, *Sox2* and *Nanog* expression relative to the monolayer control (. All samples have been normalized against GAPDH.
NB: an embryoid-like body = an aggregate of CD34+ mouse fibroblasts.

FIG. 5

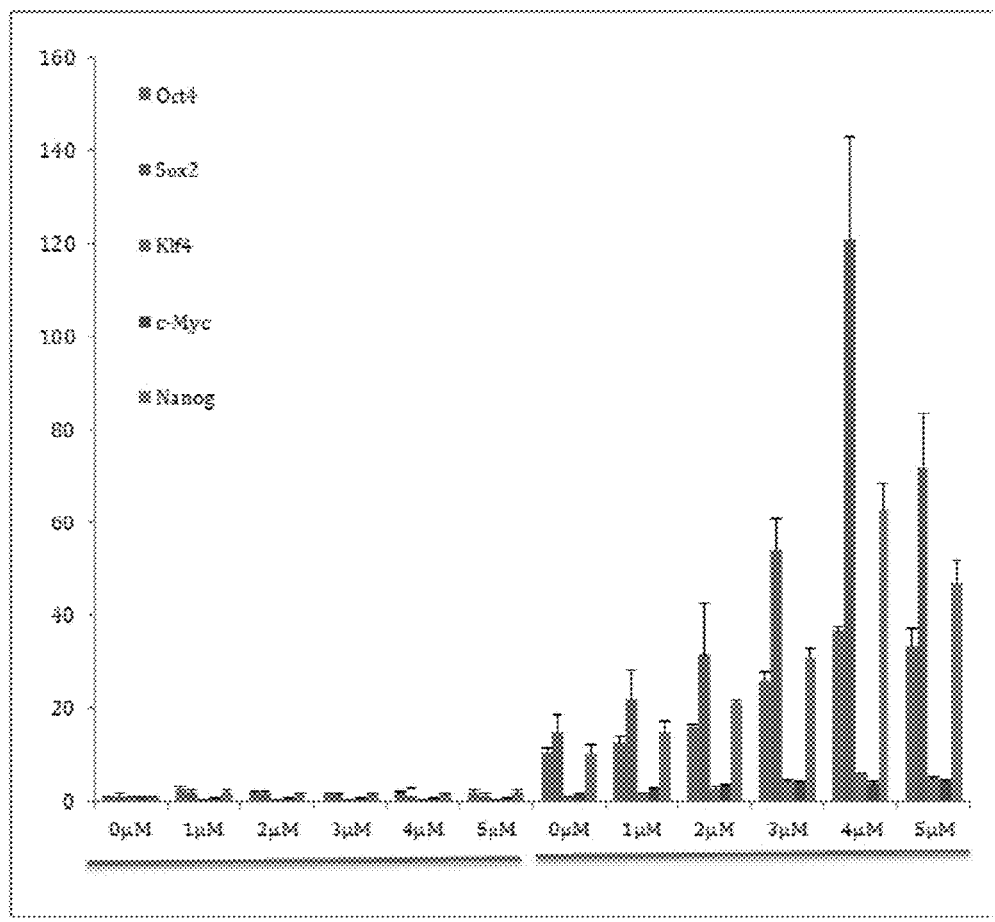

Figure 6. Human umbilical cord perivascular mesenchymal progenitor (HUCPV) cells were allowed to adhere to culture dishes and then treated with 0 - 5µM of Programin for 30 hours. RT-qPCR analysis revealed that Programin did not activate Oct4, Sox2, Klf4, c-Myc and, Nanog expressions in the monolayer HUCPV cell cultures. The physical process of aggregating the HUCPV cells into an embryoid-like body could significantly activate low levels of Oct4, Sox2 and Nanog expression. However, Klf4 and c-Myc expression were not activated. The embryoid-like bodies of HUCPV cells were treated with 1 - 5µM of Programin for 30 hours. Programin at all concentrated tested significantly activate and elevate Oct4, Sox2, Kl4, c-Myc and, Nanog expression compared with untreated embryoid-like body (0µM). The most effect dosage was determined to be 4µM Programin. Again, like for mouse fibroblasts, the HUCPV cells must be aggregated into embryoid-like bodies before they could respond to Programin. Furthermore, the embryoid-like bodies must be maintained in non-adhesive hydrophobic culture dishes, which prevented them from sticking to the dish surfaces.
Y-axis: Fold changes in Oct4, Sox2, Nanog, Kl4 and c-Myc expression relative to the monolayer HUCPV cell control. All samples have been normalized against GAPDH. NB: an embryoid-like body = an aggregate of HUCPV cells.

*FIG. 6*

Figure 7. Higher resolution of the RT-qPCR analysis in Figure 7 showing KL4 and c-Myc expression in HUCPV cells treated with 0-5µM of Progranin for 30 hours.

Y-axis: Fold changes in KL4 and c-Myc expression relative to the monolayer HUCPV cell control. All samples have been normalized against GAPDH.
NB: an embryoid-like body = an aggregate of HUCPV cells.

OCT4

Nanog

Sox2 c-MYC

KLF4

1 monolayer/ DMSO
2 monolayer/ programin
3 embryoid body-like/ DMSO
4 embryoid body-like/ programin

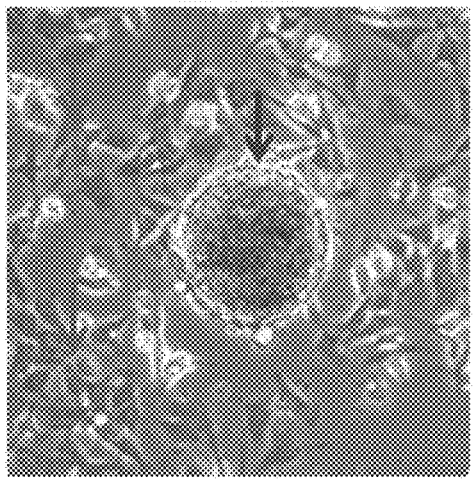
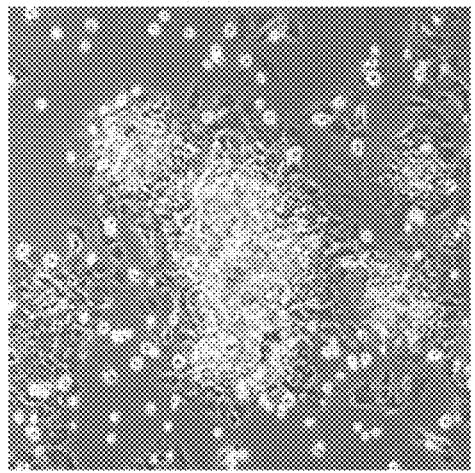
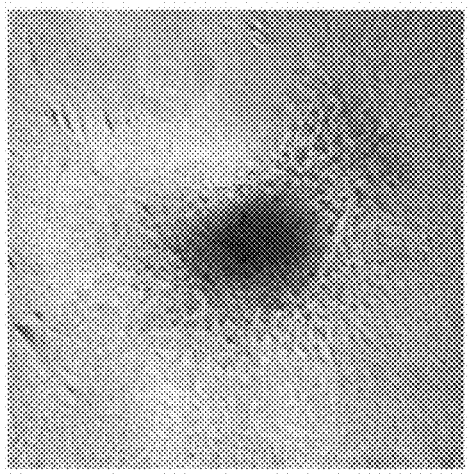
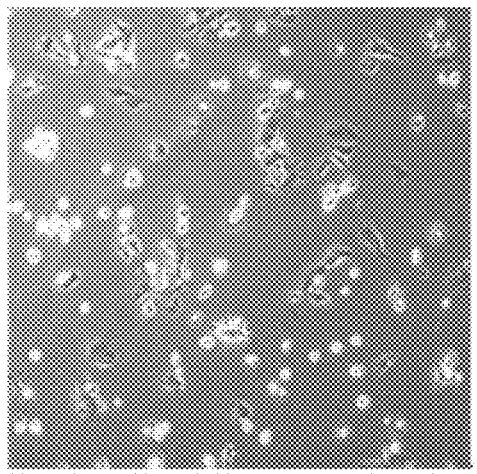

Figure 9. Developmental potential of the Programin treated mouse fibroblasts. (A) showing the typical appearance of a Programin treated mouse embryoid-like cell body (red arrow) introduced onto adhesive 0.1% gelatin coated culture dishes. Surrounding these bodies are Programin treated cells that have not formed into aggregates (green arrows). The cultures were treated with 10 µM of Wnt agonist for 2 – 3 days. (B) showing the embryoid-like cell bodies have differentiated into osteogenic nodules (*) after 2 days exposure to Wnt agonist. (C) Alizen Red S staining confirmed that the nodules formed from the embryoid-like cell bodies are osteocytes. (D) Alizen Red S staining showing the Programin treated embryoid-like cell can differentiate into osteocytes. In this case, the reprogrammed cells were induced using conventional bone inducing medium (10mM β-glycerophosphate, 50µM ascorbic acid 2-phosphate and 1µM dexamethasone) for 2 weeks.

Day 0 neural induction FIG. 10A

Day 3 neural induction FIG. 10B

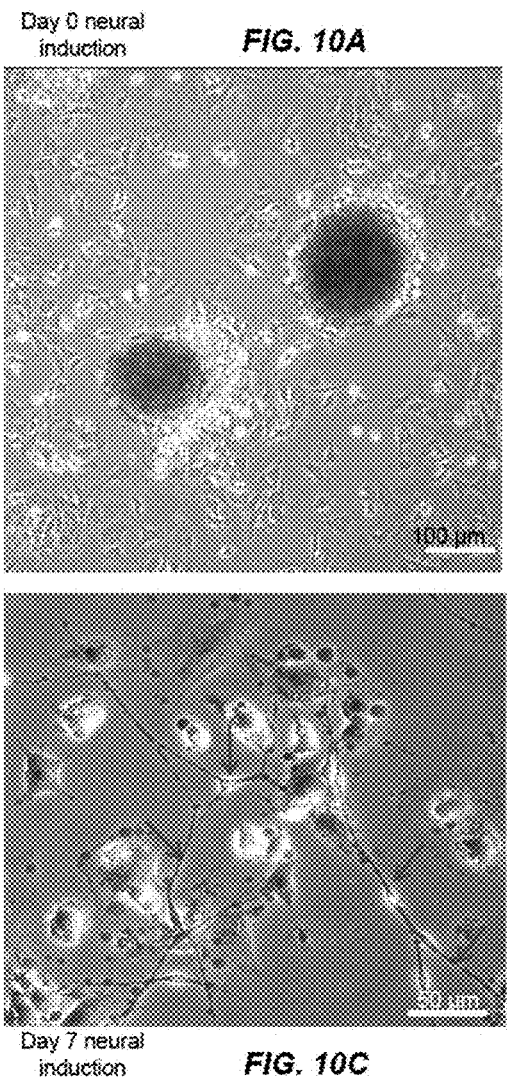
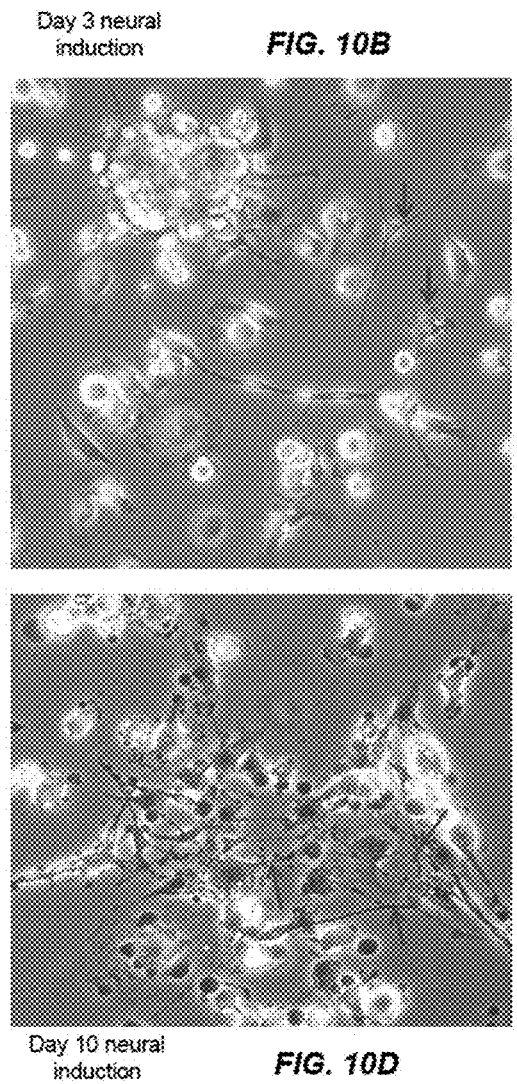

Day 7 neural induction FIG. 10C

Day 10 neural induction FIG. 10D

Fig 10. Developmental potential of the Programin treated mouse fibroblasts. (A) Representative appearance of Programin treated mouse embryoid-like cell bodies (EB) introduced into adhesive 0.1% gelatin coated culture dishes. (B) The B27 supplement present in the culture medium spontaneously induces the cells spreading from the embryoid-like cell bodies to differentiate into nerve cells (red arrows) after 3 days culture. (C and D) The presence of neurons (red arrows) were more obvious after 7 and 10 days culture, respectively.

COMBINATIONAL USE OF MECHANICAL MANIPULATION AND PROGRAMIN DERIVATIVES TO INCREASE OCT4, SOX2, OR NANOG EXPRESSION IN FIBROBLASTS

FIELD OF THE INVENTION

The present invention relates to the use of mechanical aggregation of somatic cells to form embryoid-like cell bodies as well as the treatment of these aggregates with programin or a derivative thereof to reprogram the somatic cells and produce pluripotent stem cells. Such reprogrammed cells are useful in the field of regenerative medicine.

BACKGROUND OF THE INVENTION

Stem cells have been trumpeted as the solution for alleviating the serious shortage of tissue and organs for transplantation. To date, numerous types of naturally occurring and artificially produced stem cells have been identified or created. However, every one of them has their own shortcomings. Induced pluripotent stem cells (iPSCs), produced from reprogramming of somatic cells such as skin fibroblasts (Takahashi and Yamanaka, *Cell,* 126(4):663-76 (2006)), is currently regarded as the best candidate for use in regenerative medicine. However, iPSC generation remains a very slow (~4 weeks) and inefficient (<0.01%) process that results in a heterogeneous population of cells, and requires specific expertise in human pluripotent cell culture (Takahashi et al., *Cell,* 131, 861-72 (2007); Yu et al., *Science,* 318, 1917-20 (2007)). An alternative approach is to use a small chemical molecule that can directly activate the pluripotent genes Oct4, Sox2 and Nanog.

Programin was first synthesized by Chen et al. (*J. Am. Chem. Soc.,* 2004 126: 410-411). It was used to transdifferentiate C2C12 myogenic cells into osteocytes and adipocytes. Subsequently, it was shown that the polycomb genes in C2C12 were probably involved in the transdifferentiation process using comparative proteomic techniques (Shen et al., *Proteomics,* 2007, 7(23): 4303-4316). Furthermore, it was reported that treating fibroblasts with reversine could induce them to transdifferentiate into skeletal muscle cells (Luigi et al., 2007, *Cell Death and Differentiation,* 13(12): 2042-2051; Chiara et al., 2009, *Electrophoresis,* 30(12): 2193-2206). Mandal et al. (*Biochip Journal,* 2013, 7(3): 278-287) examined the transcriptome profile of reversine-mediated transdifferentiation of NIH3T3 fibroblasts into osteoblasts. The study did not show that reversine activated the expression of pluripotency genes such as Oct4, Sox2 and Nanog.

There is a need for simple and efficient methods based on the use of small molecule compounds to generate iPSCs. The present invention meets this and other needs.

BRIEF SUMMARY OF THE INVENTION

In one aspect, the present invention provides a method for producing a pluripotent stem cell from differentiated cells. The method includes (a) culturing the differentiated cells in a vessel; (b) mechanically agitating the differentiated cells to form a cellular aggregate; (c) exposing the cellular aggregate to an effective amount of any one of the compounds of Formula II-IX having the following structures:

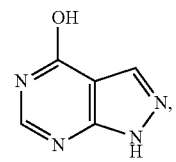
(II)

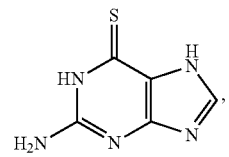
(III)

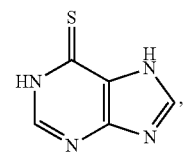
(IV)

(V)

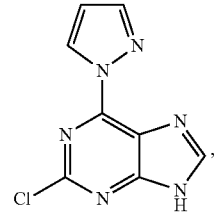
(VI)

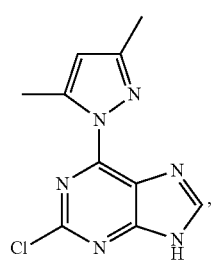
(VII)

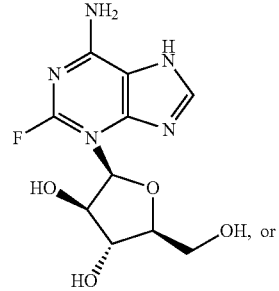
(VIII)

-continued

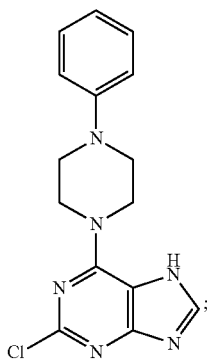
(IX)

(d) detecting the expression level of Oct4, Sox2 or Nanog in the cells of the aggregate; and (e) determining any cell is a pluripotent stem cell if the expression level of Oct4, Sox2 or Nanog in the cell of the aggregate is higher than the corresponding expression level in a differentiated cell; and (f) isolating the pluripotent stem cell. In some embodiments, step (b) and (c) are performed concurrently. In other embodiments, step (b) and (c) are performed subsequently. For example, step (c) can be performed about 24 hours to about 96 hours or more, e.g., about 24 hours, about 36 hours, about 48 hours, about 60 hours, about 72 hours, about 84 hours, about 96 hours or more, after step (b).

The differentiated cells of step (a) can be obtained from a subject or a cell line. In some embodiments, the subject is a mammalian subject. The cell line can be a mammalian cell line. In some embodiments, the differentiated cells are fibroblasts or the differentiated cells are progenitor cells. The differentiated cells of step (a) can be at a density of about $1 \times 10^5 - 1 \times 10^6$ cells/cm$^2$.

The cellular aggregate does not adhere to an inner surface of the vessel. In some embodiments, the inner surface of the vessel is coated with a non-adherent substrate (e.g., a substrate that prevents or hinders cells from adhering to it).

In some embodiments, mechanically agitating includes titurating, stirring or rocking the differentiated cells by way, e.g., shaking or rotating the culture vessel in which the cells are maintained. For example, the cells can be pipetted using a wide bore pipet tip such that mechanical force is applied to the cells or cell aggregates to prevent or hinder them from attaching to the culture vessel.

In some embodiments, step (d) of the method described above includes an amplification-based assay, a hybridization-based assay, an immunoassay or a flow cytometry assay. Subsequent to step (e), the method can also include expanding (proliferating) the pluripotent stem cell. Additionally, subsequent to step (e), the method can include inducing the pluripotent stem cell to undergo differentiation.

In some instances, the higher expression level of Oct4, Sox2 or Nanog is at least about 10 fold or about 20-fold to about 200-fold higher compared to the differentiated cell.

In another aspect of the present invention, provided herein is a pluripotent cell or cell line obtained by any one of the exemplary embodiments of the method described above.

In yet another aspect, the present invention provides a method for producing a cellular aggregate from differentiated cells, wherein the cellular aggregate comprise a cell that expresses at least one pluripotent stem cell marker. The method includes (a) culturing the differentiated cells at a density of about $1 \times 10^5$ to about $1 \times 10^6$ cells/ml in a vessel; (b) mechanically agitating the differentiated cells to form the cellular aggregate; and (c) culturing the cellular aggregate under conditions to produce a cell that expresses at least one pluripotent stem cell marker.

In some embodiments, the method also includes step (d) comprising exposing the cellular aggregate to an effective amount of a compound of Formula II-IX having any one of the following structures:

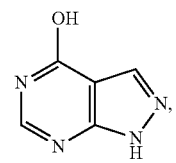
(II)

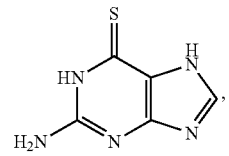
(III)

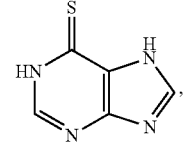
(IV)

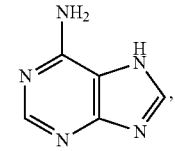
(V)

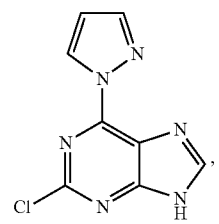
(VI)

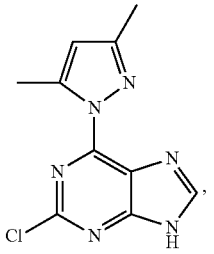
(VII)

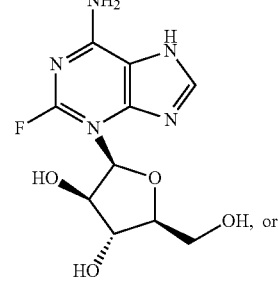
(VIII)

-continued

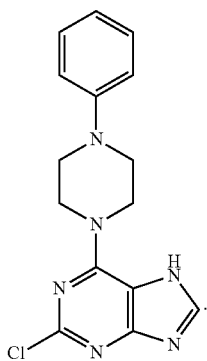
(IX)

The method can also include, subsequent to step (c), expanding the cell that expresses at least one pluripotent stem cell marker. Optionally, subsequent to step (c) the method can include isolating the cell that expresses at least one pluripotent stem cell marker. The at least one pluripotent stem cell marker can be Oct4, Sox2 or Nanog.

In another aspect, the present invention provides a compound of Formula II-IX having the any one of the following structures:

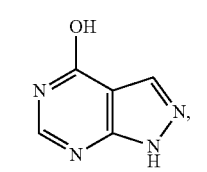
(II)

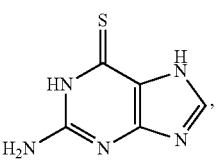
(III)

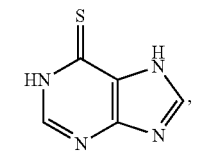
(IV)

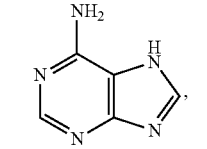
(V)

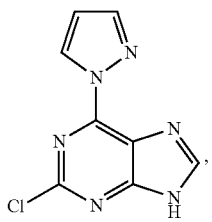
(VI)

-continued

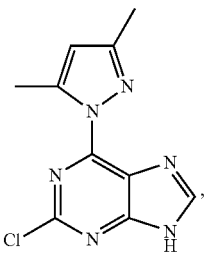
(VII)

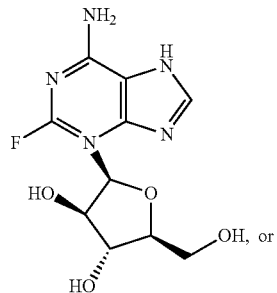
(VIII)

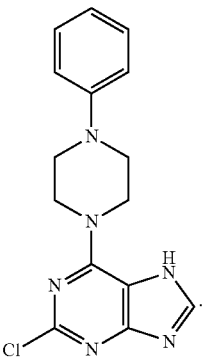
(IX)

Optionally, the compound is present in a mixture comprising differentiated cells. For instance, a compound of Formula II, III, IV, V, VI, VII, VIII or IX and the differentiated cells can be admixed together to form a mixture. In some embodiments, the differentiated cells of the mixture are present in aggregates.

In another aspect, provided herein is a pharmaceutical composition for producing a pluripotent stem cell from differentiated cells, the composition comprising a compound described above and pharmaceutically acceptable salt.

The inventors have surprising discovered that fibroblasts if mechanically formed into embryoid-like bodies and maintained on non-adhesive culture dishes over a period of 4 days, can express the pluripotency genes Oct4, Sox2 and Nanog. Furthermore, treatment of these aggregates with the small molecule compound programin or a derivative thereof increased the expression of these three pluripotent genes by 25-200-fold compared to the unaggregated, untreated differentiated cell.

BRIEF DESCRIPTION OF THE DRAWINGS

FIGS. 2A-2D show the effect of programin on mouse fibroblasts cultured as a monolayer. The fibroblasts were derived from the tail of Oct4-EGFP transgenic mice. FIG. 2A shows $CD34^+$ fibroblasts. FIG. 2B shows the absence of GFP+ fibroblasts. FIGS. 2C and 2D show fibroblasts after exposure to programin for 2 days.

FIGS. 3A-3D show the effect of programin on mouse Oct4-EGFP fibroblasts cultured in aggregates or embryoid-like bodies. FIG. 3A shows the aggregate at day 3 of culturing on a non-adherent culture plate. FIG. 3B shows an aggregate after 24-hour exposure to programin. GFP+ are detectable by microscopy. FIG. 3C shows an aggregate after 48-hour exposure to programin. FIG. 3D shows an aggregate after 96-hour exposure to programin.

FIG. 4 shows that CD34+ mouse fibroblasts cultured in a monolayer do not express Oct4, Sox2 and Nanog, as determined by qPCR. Expression of these pluripotency markers was higher in the cell aggregates and highest in the aggregates that were treated with programin.

FIG. 5 provides qPCR data showing that programin derivatives can enhance Oct4, Sox2 and Nanog expression in cell aggregates of CD34+ mouse fibroblasts. The small molecules tested include 237 (Formula II), 400 (Formula III), 594 (Formula IV), 648 (Formula VIII), 668 (Formula V), 957 (Formula IX), 958 (Formula VI), 959 (Formula VII) and programin (Formula I).

FIG. 6 shows that aggregates of human umbilical cord perivascular mesenchymal progenitor (HUCPV) cells express higher levels of Oct4, Sox2 and Nanog after treatment with 0-5 µM programin compared to similar cells cultured in a monolayer.

FIGS. 9A-9D show programin-treated aggregates (e.g., embryoid-like bodies) differentiated into osteogenic (bone) cells. FIG. 9A shows an aggregate prior to differentiation. FIG. 9B shows the cells after treatment with 10 µM Wnt agonist. Osteogenic nodules were visible after 2 days exposure to the Wnt agonist. FIG. 9C shows Alizen Rad S staining of the nodules. FIG. 9D shows that programin-treated cells that were not mechanically formed into aggregates underwent cell death.

FIGS. 10A-10D show programin-treated aggregates (e.g., embryoid-like bodies) differentiated into neural cells. FIG. 10A shows an aggregate prior to differentiation. FIG. 10B shows the cells treated with B27 supplement. FIGS. 10C and 10D show neurite outgrowths from the differentiated cells.

DETAILED DESCRIPTION OF THE INVENTION

I. Introduction

Figure 1:
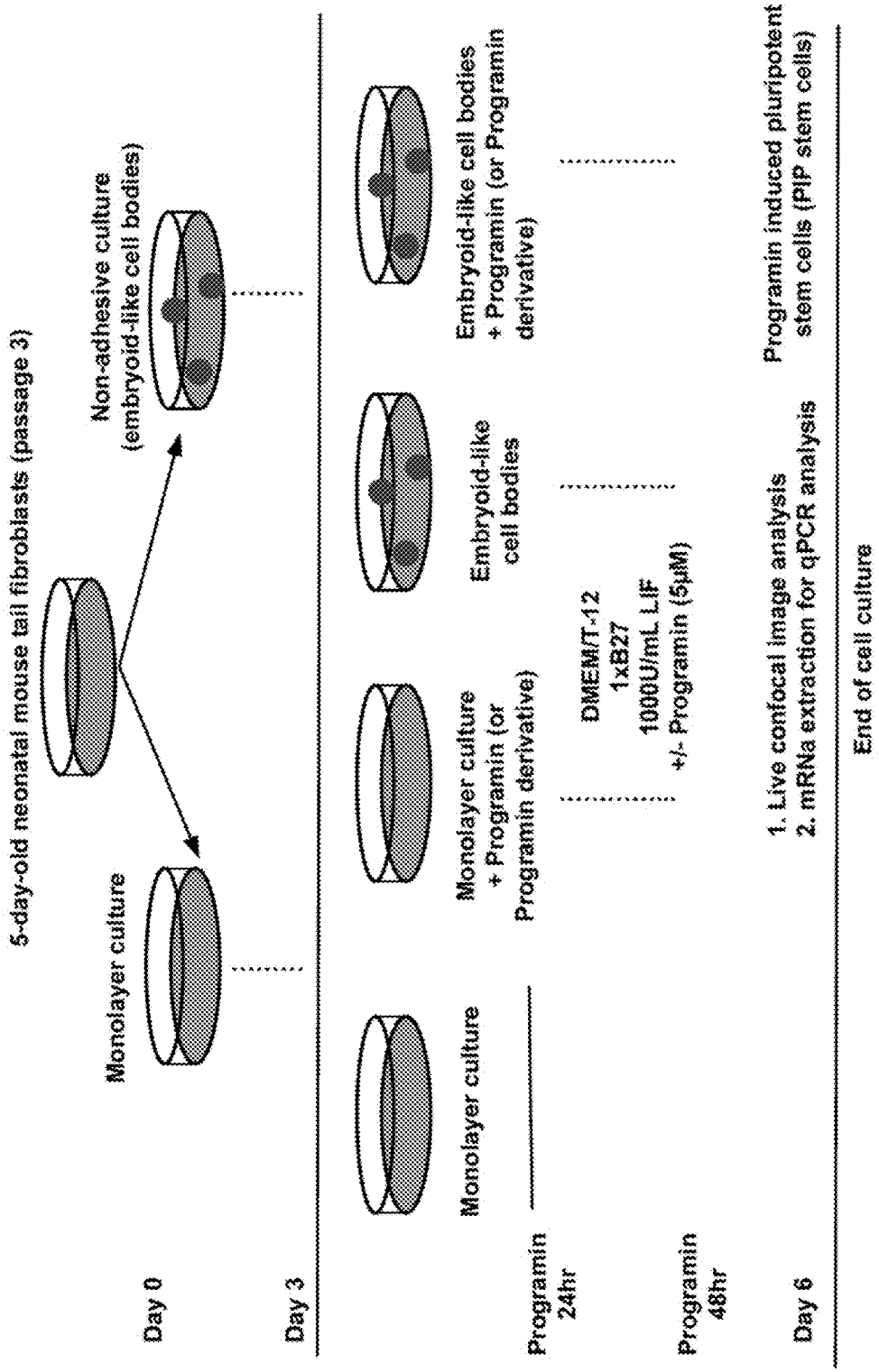
FIG. 1 shows a schematic diagram of an exemplary method for inducing pluripotency from fibroblasts.

The present invention is based, in part, on the surprising discovery that exposing cell aggregates (e.g., embryoid-like bodies) derived from somatic cells to a small molecule compound greatly improves the efficiency of induction of pluripotency in such cells. Accordingly, the present invention provides compounds, compositions and methods for dedifferentiating (e.g., reprogramming) lineage committed mammalian cells into pluripotent stem cells. More specifically, the present invention provides compounds of Formulas I-IX (e.g., programin and derivatives thereof) and are useful of dedifferentiating a lineage committed cell or for inducing pluripotent stem cells from a lineage committed cell. In addition, the methods provided herein include forming cell aggregates (e.g., embryoid-like bodies) by mechanical means. The induced pluripotent stem cells generated from the methods can be differentiated into lineage committed cells.

The present invention involves the use of programin and its derivatives to generate pluripotent stem cells from differentiated cells. The use of programin alone cannot activate expression of the pluripotency genes Oct4, Sox2, Nanog and E-Cadherin in somatic cells. The cells, such as human and mouse fibroblasts, must first be mechanically aggregated into embryoid-like cell bodies for about 4 days before they are able to respond to the reprogramming activity of programin or a derivative thereof. The cell aggregation process alone causes the fibroblasts to express basal levels of Oct4, Sox2 and Nanog. In addition, the aggregation enables the fibroblasts to respond to programin or a derivative thereof. The exposure of the embryoid-like cell bodies to 2-5 µM programin for 30 hours resulted in a 25-200 fold increase in Oct4, Sox2 and Nanog expression compared to an untreated control fibroblast.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

III. Definitions

In this disclosure the term "or" is generally employed in its sense including "and/or" unless the content clearly dictates otherwise.

The term "Oct4" or "Oct-4" refers to a transcription factor belonging to the POU family. Oct4 is a marker of undifferentiated cells (Okamoto et al., Cell 60:461-72, 1990). Oct4 is also reported to participate in the maintenance of pluripotency (Nichols et al., Cell 95:379-91, 1998). The human Oct4 polypeptide sequence are set forth in, e.g., Genbank Accession Nos. NP_001167002, NP_001272915, NP_001272916, NP_002692, and NP_0976034. The human Oct4 mRNA (coding) sequence are set forth in, e.g., Genbank Accession Nos. NM_001173531 NM_001285986, NM_001285987, NM_002701, and NM_203289. One skilled in the art will appreciate that variants, isoforms, alternative sequences of Oct4 are also useful in the present invention.

The term "Sox2" or "Sox-2" refers a member of the SRY-related HMG-box (SOX) family of transcription factors involved in regulation of embryonic development and the determination of cell fate. The human Sox2 polypeptide sequence is set forth in, e.g., Genbank Accession No. NP_003097. The human Sox2 mRNA (coding) sequence is set forth in, e.g., Genbank Accession No. NM_003106. One skilled in the art will appreciate that variants, isoforms, alternative sequences of Sox2 are also useful in the present invention.

The term "Nanog" refers to a transcription regulator involved in the proliferation and self-renewal of embryonic stem cells and the inner cell mass. The human Nanog polypeptide sequence is set forth in, e.g., Genbank Accession No. NP_0079141. The human Nanog mRNA (coding) sequence is set forth in, e.g., Genbank Accession No. NM_024865. One skilled in the art will appreciate that variants, isoforms, alternative sequences of Nanog are also useful in the present invention.

The term "pluripotent" or "pluripotency" refers to cells with the ability to give rise to progeny cells that can undergo differentiation, under the appropriate conditions, into cell types that collectively demonstrate characteristics associated with cell lineages from all of the three germinal layers (endoderm, mesoderm, and ectoderm). Pluripotent stem cells can contribute to all embryonic derived tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression of certain combinations of molecular markers are also pluripotent stem cell characteristics. For example, human pluripotent stem cells express at least some, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

The term "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and lymphocytes.

The term "lineage committed cell" refers to any cell that has or will differentiate into a particular cell type or related cell types. Lineage committed cells include, for example, osteoblasts, myoblasts, chondrocytes, neural cells, and adipocytes.

The term "dedifferentiate," "dedifferentiation," or "reprogramming" as used herein, refers to the process by which lineage committed cells (e.g., myoblasts or osteoblasts) reverse their lineage commitment and can generate progeny of a new cell type, such as a precursor cell, progenitor cell, multipotent stem cell, or pluripotent stem cell. For instance after sufficient proliferation, a measurable proportion of progeny may have phenotypic characteristics of a new cell type and this proportion is measurably more than before dedifferentiation or reprogramming. Under certain conditions, the proportion of progeny with characteristics of the new cell type may be at least about 1%, 5%, 25% or more in order of increasing preference. Dedifferentiated cells can be identified by loss of patterns of gene expression and cell surface protein expression associated with the lineage committed cells.

The term "vessel" refers to a container, dish, plate, flask, bottle, cell culture tube, and the like that can be used to culture, maintain or grow a cell.

The term "mechanically agitating" refers to applying mechanical force to an object, such as a group of cells or cell aggregates.

The term "cellular aggregate" refers to a mass of at least three cells that are in contact with each other and do not form a single layer of cells, e.g., a monolayer.

The term "culturing," as used herein, refers to maintaining cells under conditions in which they can proliferate, differentiate, and avoid senescence. Cells can be cultured in growth media containing appropriate growth factors.

As used herein, "promote" or "increase," or "promoting" or "increasing" are used interchangeably herein. These terms refer to the increase in a measured parameter (e.g., activity, expression, glycolysis, glycolytic metabolism, glucose uptake, biosynthesis downstream of glycolysis) in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit," "prevent" or "reduce," or "inhibiting," "preventing" or "reducing" are used interchangeably herein. These terms refer to the decrease in a measured parameter (e.g., activity, expression, mitochondrial respiration, mitochondrial oxidation, oxidative phosphorylation) in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is undetectable (i.e., completely inhibited) in the treated cell in comparison to the untreated cell.

The term "pharmaceutically acceptable salt" refers a salt of the active compound which is prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Programin and Derivatives Thereof

The present invention provides compounds derived from the compound known as reversine, programin, or 2-(4-Morpholinoanilino)-6-cyclohexylamino-purine. In one aspect, the compound has the Formula (I):

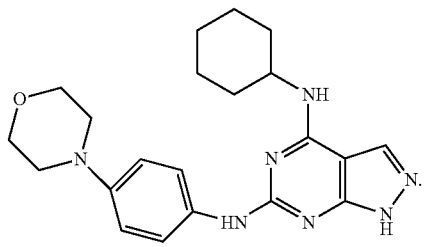 [SMILES: c1cc(N2CCOCC2)ccc1Nc1nc(NC2CCCCC2)c2cn[nH]c2n1]

In another aspect, the compound has the Formula (II):

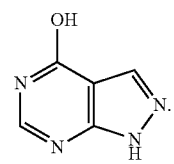

In another aspect, the compound has the Formula (III):

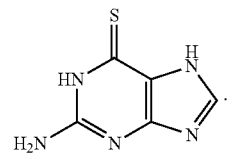

In yet another aspect, the compound has the Formula (IV):

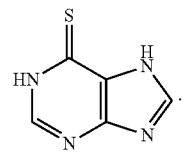

In another aspect, the compound has the Formula (V):

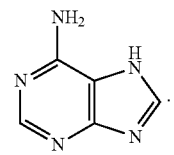

In another aspect, the compound has the Formula (VI):

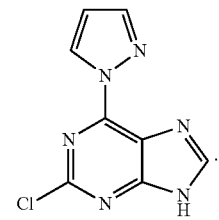

In some aspects, the compound has the Formula (VII):

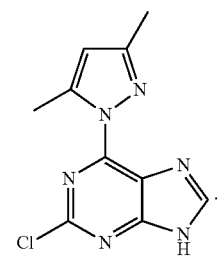

In another aspect, the compound has the Formula (VIII):

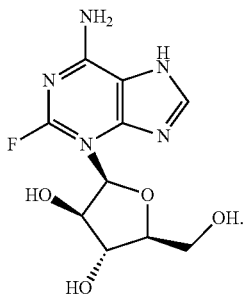

In another aspect, the compound has the Formula (IX):

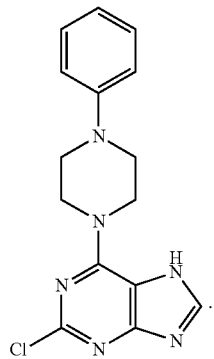

The compounds can include all pharmaceutically acceptable salts, isomers, solvates, hydrates and prodrugs thereof.

One skilled in the art recognizes that 2-(4-morpholinoanilino)-6-cyclohexylamino-purine (programin or reversine) and derivatives thereof may be prepared by either solid-phase synthesis or solution-phase synthesis. Detailed methods for synthesizing such compounds are found in, e.g., Ding et al., *J. Am. Chem. Soc.*, 124:1594 (2002); U.S. Pat. Nos. 7,176,312; 7,273,864; and 7,592,177, the disclosures are herein incorporated by reference in their entirety for all purposes.

Briefly, for solution phase synthesis of programin, cyclohexylamine and diisopropylethylamine may be added to a solution of 2-fluoro-6-chloropurine in n-butanol. The mixture may be heated to 80° C. with vigorous stirring for 12 hours. The solvent can then be removed under reduced pressure and the crude can be used directly in the next step reaction without further purification. The crude 2-fluoro-6-cyclohexylamino-purine may be dissolved in ethanol, followed by addition of 4-morpholinoaniline. The mixture may be heated to 75° C. in a sealed tube with vigorous stirring for 24 hours. The solvent may then be removed under reduced pressure and the crude material may be directly purified by flash chromatography to afford 2-(4-morpholinoanilino)-6-cyclohexylamino-purine as a pale white solid. It will be apparent to those skilled in the art that derivatives of 2-(4-morpholinoanilino)-6-cyclohexylamino-purine, such as compounds having the structure of Formulas II-IX, may be prepared via solution-phase synthesis or solid phase synthesis.

V. Reprogramming to Induce Pluripotency in Non-Pluripotent Cells

A number of different methods and protocols have been established for inducing non-pluripotent mammalian cells into induced pluripotent stem cells. iPSCs are similar to ESCs in morphology, proliferation, and pluripotency, judged by teratoma formation and chimera contribution. Reprogramming protocols include those involving the introduction of one or more reprogramming transcription factors selected from an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc).

Studies have shown that retroviral transduction of mouse fibroblasts with four transcription factors that are highly expressed in ESCs (Oct-3/4, Sox2, KLF4 and c-Myc) generate IPSCs. See, Takahashi, K. & Yamanaka, S. *Cell* 126, 663-676 (2006); Okita, K., Ichisaka, T. & Yamanaka, S. *Nature* 448, 313-317 (2007); Wernig, M. et al. *Nature* 448, 318-324 (2007); Maherali, N. et al. *Cell Stem Cell* 1, 55-70 (2007); Meissner, A., Wernig, M. & Jaenisch, R. *Nature Biotechnol.* 25, 1177-1181 (2007); Takahashi, K. et al. *Cell* 131, 861-872 (2007); Yu, J. et al. *Science* 318, 1917-1920 (2007); Nakagawa, M. et al. *Nature Biotechnol.* 26, 101-106 (2007); Wernig, M., Meissner, A., Cassady, J. P. & Jaenisch, R. *Cell Stem Cell.* 2, 10-12 (2008). Studies have also demonstrated reprogramming of human somatic cells with transcription factors that are highly expressed in ESCs: Hockemeyer et al. *Cell Stem Cell.* 11; 3(3):346-53 (2008); Lowry et al. *Proc Natl Acad Sci USA.* 105(8):2883-8 (2008); Park et al. *Nature.* 10; 451(7175):141-6 (2008); Nakagawa et al. *Nat Biotechnol.* January; 26(1):101-6 (2008); Takahashi et al. *Cell.* 131(5):861-72 (2007); and Yu et al. *Science.* 318(5858):1917-20 (2007).

It has been shown that the efficiency of reprogramming (e.g., the number of reprogrammed cells) can be enhanced by the addition of various small molecules as shown by, e.g., Shi, Y., et at (2008) Cell-Stem Cell 2:525-528, Huangfu, D., et at (2008) Nature Biotechnology 26(7):795-797, Marson, A., et at (2008) Cell-Stem Cell 3:132-135. It is contemplated that the methods described herein can also be used in combination with additional single small molecule (or a combination of small molecules) that enhances the efficiency of production or a reprogrammed cell. In some embodiments, some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), and trichostatin (TSA), among others. It is also contemplated herein that inhibitors of the TGF-β signaling pathway (e.g. Repsox, E-616451 or SB431542, and anti-TGFβ antibodies or RNAi agents) or inhibitors of SRC signaling, such as EI-275, or agonist of MEK/ERK cell signaling (e.g., prostaglandin 2); inhibitors of $Ca^{2+}$/calmodulin signaling or EGF receptor tyrosine kinase inhibitor; inhibitors of $Na^{2+}$ channels or ATP-dependent potassium channel or agonists of MAPK signaling pathway can be used either alone or in combination with another small molecule (or combination of small molecules) to enhance or increase the efficiency of producing reprogrammed cells from differentiated cells as disclosed herein. Additional agents include PDK1 activators or compounds that promote glycolytic metabolism, and/or Rho GTPase/ROCK inhibitors.

It is believed that the small molecules described herein can be used in combination with essentially any method for generating iPSCs and thereby improve the efficiency of the method.

A. Obtaining Non-Pluripotent Cells and Culturing

Non-pluripotent mammalian cells that can be used to generate iPSCs according to the methods described herein can be differentiated cells from any suitable mammal (e.g., rodents such as, for example, mice, rats, guinea pigs, and rabbits; non-rodent mammals such as, for example, dogs, cats, pigs, sheep, horses, cows, and goats; primates such as, for example, chimpanzees and humans).

Differentiated cells are any cells forming the body of an organism, as opposed to germline cells (e.g., gametes includes spermatozoa and ova). Every other cell type in the mammalian body (apart from the sperm and ova, gametocytes and undifferentiated stem cells) is a differentiated cell.

The cell can be, e.g., in culture or in a tissue, fluid, etc. and/or from or in an organism. In some embodiments, the differentiated cell is a primary cell line or is the progeny of a primary or secondary cell line. Cells that can be induced to pluripotency include, but are not limited to, fibroblast cells, blood cells, e.g., T cells, B cells, monocytes, myeloid progenitor cells, etc., fibroblast cells, tumor cells, bone marrow cells, stomach cells, liver cells, epithelial cells, nasal epithelial cells, mucosal epithelial cells, follicular cells, connective tissue cells, muscle cells, bone cells, cartilage cells, gastrointestinal cells, splenic cells, kidney cells, lung cells, testicular cells, and nervous tissue cells. In some embodiments, the human cell is a fibroblast, which may be conveniently obtained from a subject by a punch biopsy. In other embodiments, the human cell is obtained from a sample, e.g., a hair follicle, a blood sample, a swab sample (e.g., an oral swab sample), and the like. When the reprogrammed cells (e.g. induced pluripotent stem cells) are used for therapeutic treatment of diseases, it is desirable to use differentiated cells (e.g. somatic cells) isolated from patients.

Methods for isolation and culture of human and mammalian cells are well known in the art and have been described in, e.g., Humason, ANIMAL TISSUE TECHNIQUES, 4.sup.th ed., W. H. Freeman and Company (1979); Freshney et al., CULTURE OF ANIMAL CELLS (3rd ed. 1994); and Ricciardelli et al., (1989) In Vitro Cell Dev. Biol. 25: 1016.

Suitable cell culture methods and conditions can be determined by those of skill in the art using known methodology (see, e.g., Freshney et al., 1994, supra). In general, the cell culture environment includes consideration of such factors as the substrate for cell growth, cell density and cell contract, the gas phase, the medium, and temperature. Incubation of cells is generally performed under conditions known to be optimal for cell growth. Such conditions may include, for example, a temperature of approximately 37° C. and a humidified atmosphere containing approximately 5% $CO_2$. The duration of the incubation can vary widely, depending on the desired results. In general, incubation is preferably continued until the cells express suitable Proliferation is conveniently determined using: $^3H$ thymidine incorporation or BrdU labeling. Plastic dishes, flasks, or roller bottles may be used to culture cells according to the methods of the present invention. Suitable culture vessels include, for example, multi-well plates, petri dishes, tissue culture tubes, flasks, roller bottles, and the like.

Defined cell media are available as packaged, premixed powders or presterilized solutions. Examples of commonly used media include MEM-α DME, RPMI 1640, DMEM, Iscove's complete media, or McCoy's Medium (see, e.g., GibcoBRL/Life Technologies Catalogue and Reference Guide; Sigma Catalogue). Typically, MEM-α or DMEM are used in the methods of the invention. Defined cell culture media are often supplemented with 5-20% serum, typically heat inactivated serum, e.g., human, horse, calf, and fetal bovine serum. Typically, 10% fetal bovine serum is used in the methods of the invention. The culture medium is usually buffered to maintain the cells at a pH preferably from about 7.2 to about 7.4. Other supplements to the media typically include, e.g., antibiotics, amino acids, and sugars, and growth factors.

B. Forming Cell Aggregates

To induce pluripotency, the somatic cells are cultured in suspension to form embryoid-like bodies. In some embodiments, the somatic cells are suspended at a density of about $1\times10^5$ cells/cm$^2$ to about $1\times10^6$ cells/cm$^2$. In other embodiments, the cells are at a density of about 30,000 cells/ml to about 500,000 cells/ml. The cells can be cultured in a non-adherent culture vessel, such as a non-tissue culture treated vessel or a low cell binding vessel. The cell can be grown in any vessel that prevents the cells from forming a monolayer.

To form aggregates or embryoid-like bodies, the somatic or non-pluripotent cells are cultured in suspension under conditions that allow the cells to develop into a loosely compact mass of cells. In some instances, a suspension of cells is mechanically manipulated, such as mixed, stirred, spun, titurated, and pipetted, such that the cells clump together into discrete three-dimensional aggregates. The cells can be cultured in a vessel, e.g., roller bottle or stir bottle, and periodically or continually agitated to promote the formation of aggregates.

A mechanical force can be applied to the somatic cells to prevent or hinder the cells from adhering to the surface of the culture vessel. The magnitude of the mechanical force should not alter the integrity of the cells or induce cell death. Yet, the force should be sufficient to detach isolated cells and aggregates from the surface of a non-adherent culture vessel.

The aggregates can be formed and cultured for about 2 to about 5 days, e.g., about 2 days, about 3 days, about 4 days, or about 5 days, after the start of the aggregation and before small molecule treatment.

C. Culturing Aggregates in Programin Compounds

To induce pluripotency, the aggregates can be treated with (e.g., exposed to or cultured in) a derivative of programin (compound of Formula I). In some embodiments, about 0 μM to about 10 μM, e.g., about 0 μM, about 1 μM, about 2 μM, about 3 μM, about 4 μM, about 5 μM, about 6 μM, about 7 μM, about 8 μM, about 9 μM, or about 10 μM, of a derivative of programin is used to treat the aggregates to induce pluripotent stem cells. In some embodiments, about 0 μM to about 10 μM, e.g., about 0 μM, about 1 μM, about 2 μM, about 3 μM, about 4 μM, about 5 μM, about 6 μM, about 7 μM, about 8 μM, about 9 μM, or about 10 μM, of the small molecule compound of Formula II is used to treat the aggregates to induce pluripotency. In some embodiments, about 0 μM to about 10 μM, e.g., about 0 μM, about 1 μM, about 2 μM, about 3 μM, about 4 μM, about 5 μM, about 6 μM, about 7 μM, about 8 μM, about 9 μM, or about 10 μM, of the small molecule compound of Formula III is used to treat the aggregates to induce pluripotency. In some embodiments, about 0 μM to about 10 μM, e.g., about 0 μM, about 1 μM, about 2 μM, about 3 μM, about 4 μM, about 5 μM, about 6 μM, about 7 μM, about 8 μM, about 9 μM, or about 10 μM, of the small molecule compound of Formula IV is used to treat the aggregates to induce pluripotency. In some embodiments, about 0 μM to about 10 μM, e.g., about 0 μM, about 1 μM, about 2 μM, about 3 μM, about 4 μM, about 5 μM, about 6 μM, about 7 μM, about 8 μM, about 9 μM, or about 10 μM, of the small molecule compound of Formula V is used to treat the aggregates to induce pluripotency. In some embodiments, about 0 µM to about 10 µM, e.g., about 0 µM, about 1 µM, about 2 µM, about 3 µM, about 4 µM, about 5 µM, about 6 µM, about 7 µM, about 8 µM, about 9 µM, or about 10 µM, of the small molecule compound of Formula VI is used to treat the aggregates to induce pluripotency. In some embodiments, about 0 µM to about 10 µM, e.g., about 0 µM, about 1 µM, about 2 µM, about 3 µM, about 4 µM, about 5 µM, about 6 µM, about 7 µM, about 8 µM, about 9 µM, or about 10 µM, of the small molecule compound of Formula VII is used to treat the aggregates to induce pluripotency. In some embodiments, about 0 µM to about 10 µM, e.g., about 0 µM, about 1 µM, about 2 µM, about 3 µM, about 4 µM, about 5 µM, about 6 µM, about 7 µM, about 8 µM, about 9 µM, or about 10 µM, of the small molecule compound of Formula VIII is used to treat the aggregates to induce pluripotency. In some embodiments, about 0 µM to about 10 µM, e.g., about 0 µM, about 1 µM, about 2 µM, about 3 µM, about 4 µM, about 5 µM, about 6 µM, about 7 µM, about 8 µM, about 9 µM, or about 10 µM, of the small molecule compound of Formula IX is used to treat the aggregates to induce pluripotency.

In some embodiments, the compound of Formula II-IX is exposed to the aggregate at least 8 hours, e.g., about 8 hours, 12 hours, 24 hours, 36 hours, 48 hours, 60 hours, 72 hours, 84 hours, 96 hours or more. The aggregate can be treated with any one of the compounds of Formula I-IX for at least 1 day, e.g., 1 day, 2 days, 3 days, 4 days, 5 days 6, days, 7 days, 8 days, 9 days, 10 days or more.

The aggregate can be treated with any one of the compounds of Formula I-IX, or a combination of one or more compounds of Formula I-IX. For instance, 2 compounds of Formula I-IX, such as those of Formulas I and II, Formulas I and III, Formulas I and IV, Formulas I and V, Formulas I and VI, Formulas I and VII, Formulas II and III, Formulas II and IV, Formulas I and V, Formulas II and VI, Formulas II and VII, Formulas II and VIII, Formulas II and IX, and the like can be used. In some embodiments, at least 2, e.g., 2, 3, 4, 5, 6, 7, 8 or 9, different compounds of Formula I-IX are useful for inducing pluripotency in the aggregates.

Reprogramming efficiency may be increased by 5%, 10%, 20%, 30%, 40%, 50%, 60%, 70%, 80%, 90%, 100%, 150%, 200%, 300%, 400%, 500% or more as compared with conventional methods. In some instances, the reprogramming efficiency may be as high as 1%, 2%, 3%, 4%, 5%, 6%, 7%, 8%, 9%, 10%, 20%, 30%, 40% or 50% (e.g., percent of induced pluripotent cells compared to total number of starting somatic cells).

Culturing of induced pluripotent stem cells generated in this invention can use various media and techniques developed to culture primate pluripotent stem cells, more specially, embryonic stem cells, as described in U.S. Pat. No. 7,442,548. It is appreciated that additional methods for the culture and maintenance of human pluripotent stem cells, as would be known to one of skill, may be used with the present invention. In certain embodiments, undefined conditions may be used; for example, pluripotent cells may be cultured on fibroblast feeder cells or a medium which has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwi g et al., 2006b). Feeder-independent culture systems and media may be used to culture and maintain pluripotent cells. As described herein, various modifications may be made to these methods in order to reduce costs as desired.

For example, like human embryonic stem cells, iPS cells can be maintained in 80% DMEM (Gibco #10829-018 or #11965-092), 20% defined fetal bovine serum (FBS) (or human AB serum), 1% non-essential amino acids, 1 mM L-glutamine, and 0.1 mM β-mercaptoethanol. Alternatively, iPS cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM β mercaptoethanol. Human bFGF may be added to a final concentration of about 4 ng/mL or zebrafish bFGF may be used instead.

D. Methods of Characterizing Pluripotent Stem Cell

Chemically induced reprogrammed cells as disclosed herein are indistinguishable from embryonic stem cell or other pluripotent cells in morphology, proliferation, gene expression, and teratoma formation. For example, chemically induced human reprogrammed cells are expandable and indistinguishable from human embryonic stem cells in morphology and proliferation. Furthermore, these chemically-induced reprogrammed cells can differentiate into cell types of the three germ layers in vitro and in teratomas.

Analysis to assess the pluripotency characteristics of the reprogrammed cells may be performed. The cells may be analyzed for different growth characteristics and embryonic stem cell like morphology. The pluripotent stem cells derived according to the methods described herein have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of stem cells can also be confirmed by injecting approximately 0.5-10× $10^6$ cells into the rear leg muscles of 8-12 week old male SCID mice. The appearance of teratomas demonstrate that the stem cells are differentiate to become at least one cell type of each of the three germ layers.

Expression profiling of individual genes associated with pluripotency may also be examined. Additionally, expression of embryonic stem cell surface markers may be analyzed. Detection and analysis of a variety of genes or gene products known in the art to be associated with pluripotent stem cells may include analysis of genes or gene products, such as, but not limited to, Oct4, Nanog, Sox2, Klf4, c-Myc, ABCG2, E-cadherin, β-tubulin III, α-smooth muscle actin (α-SMA), fibroblast growth factor 4 (FGF4), Cripto, Dax1, zinc finger protein 296 (Zfp296), N-acetyltransferase-1 (Nat1), ES cell associated transcript 1 (ECAT1), ESG1/DPPA5/ECAT2, ECAT3, ECAT6, ECAT7, ECAT8, ECAT9, ECAT10, ECAT15-1, ECAT15-2, Fthll7, Sall4, undifferentiated embryonic cell transcription factor (Utf1), Rex1, p53, G3PDH, telomerase, including TERT, silent X chromosome genes, Dnmt3a, Dnmt3b, TRIM28, F-box containing protein 15 (Fbx15), Esrrb, TDGF1, GABRB3, Zfp42, FoxD3, GDF3, CYP25A1, developmental pluripotency-associated 2 (DPPA2), T-cell lymphoma breakpoint 1 (Tcl1), DPPA3/Stella, DPPA4, as well as other general markers for pluripotency, for example any gene or gene product used during induction to reprogram the cell.

The cells can also be characterized by the down-regulation of markers characteristic of the differentiated cells from which the pluripotent cells are induced. Non-limiting examples of markers of endoderm cells include Gata4, FoxA2, PDX1, Nodal, Sox7 and Sox17; markers of mesoderm cells include Brachycury, GSC, LEF1, Mox1 and Tie1; and markers of ectoderm cells include Cripto1, EN1, GFAP, Islet 1, LIM1 and Nestin. Antibodies to markers of the three germ layers are commercially available from, e.g., Abcam, EMD Millipore, Santa Cruz Biotechnology, and the like.

In some embodiments, the expression level (e.g., amount) of Oct4, Nanog and Sox2 in the reprogrammed cell is at least about at least about 2-fold higher, at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, or more than the expression level (amount) of the same gene or gene product in a differentiated cell from which the reprogrammed cell was derived.

E. Methods of Enriching and/or Isolating Reprogrammed Cells

Another aspect of the present invention relates to the isolation of a population of reprogrammed cells from a heterogeneous population of cells, such a mixed population of cells comprising reprogrammed cells and differentiated cells from which the reprogrammed cells were derived. A population of reprogrammed cells produced by any of the method described herein can be enriched, expanded, isolated and/or purified by using any cell surface marker present on the reprogrammed cell which is not present on the differentiated cell from which it was derived. Such cell surface markers are also referred to as an affinity tag which is specific for reprogrammed cells. Examples of affinity tags specific for reprogrammed cells are antibodies, ligands or other binding agents that are specific to a marker molecule, such as a polypeptide, that is present on the cell surface of a reprogrammed cell but which is not substantially present on other cell types (e.g. on differentiated cells). In some methods, an antibody which binds to a cell surface antigen on a reprogrammed cell (e.g. a human reprogrammed cell) is used as an affinity tag for the enrichment, isolation or purification of chemically induced reprogrammed cells produced by the methods described herein. In some embodiments, the reprogrammed cells can also be isolated from the differentiated cells by fluorescence activated cell sorting (FACS), affinity-based methods, and a combination thereof.

The chemically induced reprogrammed cells can also be isolated by other techniques for cell isolation. Additionally, reprogrammed cells can also be enriched or isolated by methods of serial subculture in growth conditions which promote the selective survival or selective expansion of the reprogrammed cells. Such methods are known by persons of ordinary skill in the art.

In some embodiments, the cell culture or cell population comprising the reprogrammed cells comprise at least about 1% to 100%, e.g., at least about at least about 1%, at least about 2%, at least about 3%, at least about 4%, at least about 5%, at least about 6%, at least about 7%, at least about 8%, at least about 90%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, pluripotent stem cells.

F. Methods of Differentiating Reprogrammed Cells

Another method for assessing the pluripotency of the induced stem cells is to in vitro differentiate the cells into specific somatic cell types. For example, certain growth factors known to drive differentiation into particular cell types may be used.

In some embodiments, the stem cells generated according to the methods of the present invention are subsequently induced to form, for example, hematopoietic (stem/progenitor) cells, neural (stem/progenitor) cells (and optionally, more differentiated cells, such as subtype specific neurons, oligodendrocytes, etc.), pancreatic cells (e.g., endocrine progenitor cell or pancreatic hormone-expressing cells), hepatocytes, cardiovascular (stem/progenitor) cells (e.g., cardiomyocytes, endothelial cells, smooth muscle cells), retinal cells, etc. A variety of methods are known for inducing differentiation of pluripotent stem cells into desired cell types. A non-limiting examples of methods for inducing differentiation of stem cells into various cell fates are described in, for example, U.S. Pat. Nos. 8,187,878; 7,781,214; 7,757,762; 7,541,186; Kaiming Ye and Sha Jin, eds., *Human Embryonic and Induce Pluripotent Stem Cells: Lineage-specific Differentiation Protocols*, New York: Humana Press, 2011; and Schlaeger et al., *Current Protocols in Stem Cell Biology*, New York: Wiley, 2014.

G. Pharmaceutical Formulations

When used for pharmaceutical purposes, the small molecule compound of the present invention is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable salt or carrier can contain a physiologically acceptable compound that acts, for example, to stabilize the small molecule compound. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

VI. Examples

The following examples are offered to illustrate, but not to limit the claimed invention.

Example 1: Protocol for Activating Pluripotent Gene Expression in Mouse Somatic Cell We have identified a small molecule via high-through-put screening of embryoid-like bodies fabricated from fibroblasts which carried the transgene Oct4 promoter linked to an EGFP reporter (Oct4-EGFP). This synthetic heterocyclic molecule, which we named "programin" (e.g., reversine), could induce mouse somatic cells to strongly express Oct4, Sox2 and Nanog by 25-200 fold. In addition, the expression of E-cadherin (a cell adhesion gene that is crucial for maintaining pluripotency in embryonic cells) was induced and was increased by 5-fold compared to that of the initial fibroblast. The reprogramming efficiency was approximately 20% and takes 7 days to accomplish. The expression of Oct4, Sox2 and Nanog was not induced (activated) when the fibroblasts were conventionally grown on normal adhesive culture dishes as a monolayer.

The process of forming these bodies itself activates low basal levels of Oct4, Sox2 and Nanog expression (2-fold higher compared to growing, culture dish-adherent fibroblasts). This mechanically-induced bioactivity was validated by qPCR analysis. Treating the cell aggregates with programin further increased the expression of these three pluripotent genes, for example, by 20-200-fold compared to controls. These results have also been replicated many times and also using human fibroblasts. In summary, programin or derivatives thereof alone cannot active Oct4, Sox2 and Nanog expression unless the somatic cells are mechanically induced to aggregate and prevented from adhering to culture dishes.

The programin-induced pluripotent (PIP) stem cells are capable of forming osteocytes when induced by osteogenic inducing medium, as well as neural cells when treated with neural inducing supplements. This novel approach for producing pluripotent stem cells is simple, fast, efficient and cost effective. As such, PIP stem cells provide a valuable and versatile source of cells for use in generating organs and tissue transplants for use in regenerative medicine. Furthermore, human PIP stem cells can be induced to differentiate into specific cell types such as liver, heart and nerve cells for toxic and bioactivity testing of drugs by the pharmaceutical industry.

This example illustrates the use of a novel compound that enables reprogramming of mouse somatic cells into induced pluripotent stem cells (iPSCs) that express pluripotent stem cell markers.

Materials required: Culture medium, supplemented with 10% FBS, 1% PS in DMEM (Invitrogen); Mouse ESC medium, supplemented with 1×B27 (Invitrogen), 1,000 U/mL Mouse Leukemia Inhibitory Factor (LIF) in DMEM/F12 culture medium (Invitrogen); Programin (frozen stock dissolved in DMSO); Working concentration=1-5 µM; Sterile 35 mm non-adhesive culture dish (SPL; 11035).

Procedures:

Day 1 of PIP stem cells production:

1. Source mouse tail fibroblasts (passage 2-6 and in log phase of growth). Trypsinize the fibroblasts using standard protocols to obtain a suspension of the cells in culture medium.

2. Seed the fibroblasts or other somatic cells onto a sterile 35 mm non-adhesive culture dish at density of $1\times10^5$ $1\times10^6$ cells/cm$^2$ in 3 mL of culture medium.

3. Incubate the cells at 37° C. and 5% $CO_2$ inside a cell incubator.

4. Gently pipette the culture media to prevent the cells from adhering to culture dish surface. Two sessions per day, 2 min for each session, must be performed. A standard 1 mL pipette and plastic tip was used for pipetting the cultures. The pipetting has to done very slowly (approximately 0.5-1 mL/second generates sufficient force to detach cells from non-adhesive culture dish surface).

Day 2 of PIP stem cell production.

1. The cells would start to aggregate into embryoid-like bodies after day 1. These bodies will grow in numbers and size during the period of culture.

2. Gently pipette the culture media to prevent the embryoid-like cell bodies from attaching on culture dish surface.

3. Add 1 mL of fresh culture medium.

Day 4 of PIP stem cell production.

1. Collect cell suspension and pellet cells by centrifugation at 800 rpm for 5 min. Gentle centrifugation and pipetting do not de-aggregate the embryoid-like bodies. Wash cell once with mouse ESC medium and Programin (1-5 µM) or programin derivatives.

2. Pellet the embryoid-like bodies again and re-suspend them in 3 mL mouse ESC medium and Programin or derivatives thereof.

3. Seed the embryoid-like cell bodies onto a sterile 35 mm non-adhesive culture dish. Incubate the embryoid-like bodies at 37° C. and 5% $CO_2$ inside a cell incubator for 2-3 days.

4. Perform daily pipetting twice in a day to prevent the embryoid-like cell bodies from sticking to the culture dish.

5. Add 1 mL of fresh mouse ESC medium on day 5 (day 2 post-Programin treatment).

Day 6-7 of PIP stem cell production.

1. Harvest the embryoid-like cell bodies for PI and Hoechst staining for confocal analysis. The presence of green fluorescence and Hoechst staining in cells indicate the presence of live PIP cells expressing Oct4-EGFP.

2. Harvest the embryoid-like cell bodies for qPCR analysis to validate expression of pluripotent genes: Oct4, Sox2 and Nanog expression. In addition, expression of other key stem cell-associated genes.

Results:

A schematic diagram of an exemplary method of the present invention is provided in FIG. 1. Tail fibroblasts extracted from the tail of Oct4-EGFP transgenic mice and stained with CD34 (FIG. 2). The cells were sorted by flow cytometry for only those expressing the surface marker CD34. FIG. 2B shows CD34$^+$ fibroblasts grown on adhesive culture dishes for 3 days. CD34$^+$ fibroblasts grown on adhesive culture dishes and treated with 5 µM programin for 3 days died and did not express Oct4 (FIGS. 2C and 2D).

CD34$^+$ fibroblasts harvested from the tail of an Oct4-EGFP transgenic mouse were mechanically pipetted and maintained on non-adhesive culture plates so that the cells became aggregated to form embryoid-like bodies (FIG. 3A). The embryoid-like bodies in this study were stained with PI dye to determine the presence of dead cells (red arrows) and Hoechst dye for the presence of live cells (blue arrows) (FIGS. 3A-3D). Under the confocal microscope, Oct4-EGFP expression (green arrows) was undetectable in the live cells of non-treated embryoid-like bodies (FIG. 3A). Embryoid-like cell bodies treated with 5 µM of Programin for 24 hours (FIG. 3B), 48 hours (FIG. 3C), and 69 hours (FIG. 3D) expressed Oct4-EGFP. Programin was able to activate Oct4-EGFP expression (green arrows) in the CD34$^+$ fibroblasts 24-69 hours after treatment.

The qPCR results show that CD34$^+$ mouse fibroblasts when cultured as a monolayer do not express Oct4, Sox2 and Nanog (FIG. 4). In contrast, when the fibroblasts are mechanically manipulated to form embryoid-like cell bodies, they are induced to express pluripotent genes, such as Oct4, Sox2 and Nanog at low basal levels. Upon treating these embryoid-like cell bodies with 5 µm Programin, Oct4, Sox2 and Nanog expression is significantly enhanced.

The qPCR results show the efficacy of various Programin derivatives to enhance Oct4, Sox2 and Nanog expression (FIG. 5). Derivatives 237, 400, 594, 648, 668, 957, 958 and 959 significantly increased Oct4, Sox2 and Nanog expression in embryoid-like cell bodies of CD34$^+$ mouse fibroblasts. Levels of the pluripotent stem cell markers were higher in the embryoid-like cell bodies treated with programin or derivatives thereof, compared to untreated embryoid-like cell bodies and CD34+ mouse fibroblasts cultured as a monolayer.

Example 2: Protocol for Activating Pluripotent Gene Expression in Human Umbilical Cord Peri-Vascular Mesenchymal Progenitor Cells This example illustrates the use of a novel compound that promotes reprogramming of human progenitor cells, e.g., human umbilical cord peri-vascular mesenchymal progenitor cells into iPSCs that express pluripotent stem cell markers.

Materials required: HUCPV medium, consisting of 15% ESQ-FBS (Invitrogen) and 1% PS in MEM/F12 (Invitrogen), Essential 6 (Invitrogen) supplemented with 100 ng/mL basic fibroblast growth factor (bFGF) (Invitrogen), Programin or derivatives thereof (frozen stock dissolved in DMSO); Working concentration=1-5 µM; Sterile non-adhesive 24-well culture plate (SPL; 32024).

Procedures:
1. Primary human umbilical cord peri-vascular (HUCPV) cells were maintained in HUCPV culture medium and passaged by trypsinization. Only HUCPV cells below cell passage 6 were used.
2. HUCPV cultures are trypsinize and dissociate into single cells.
3. The dissociated HUCPV cells are re-suspend as $3\times10^5$ cells in 600 µL of HUCPV medium and seeded into each well of a non-adhesive 24-well culture plate.
4. The cells are incubated at 37° C. and 5% $CO_2$ inside a cell incubator.
5. On following day, until the end of experiment, the cells were pipetted twice a day to prevent cells attaching onto culture plates which caused the HUCPV cells to aggregate into embryoid-like cell bodies.
6. 200 µL of fresh HUCPV medium were added to the cultures, every 2 days.
7. After 4 days culture, the embryoid-like cell bodies were centrifuged at 800 rpm for 5 min to remove the culture medium. Ensure that centrifugation and pipetting are gentile which do not disaggregate the embryoid-like bodies.
8. Wash embryoid-like cell bodies once with HUCPV medium supplemented with Essential 6 and 1-5 µM Programin or derivatives thereof. Remove medium by centrifugation
9. Re-suspend the embryoid-like bodies in 600 µL of HUCPV medium supplemented with Essential 6 and 1-5 µM Programin or derivatives thereof into each of the wells of a sterile non-adhesive 24-well culture plate.
10. Thirty hours after Programin treatment, the Programin treated embryoid-like cell bodies were harvested for qPCR analysis to validate expression of the pluripotent genes: Oct4, Sox2 and Nanog. Other key stem cells-associate genes were also analyzed.

Results:
Human umbilical cord perivascular mesenchymal progenitor (HUCPV) cells were allowed to adhere to culture dishes and then were treated with 0-5 µM of Programin for 30 hours. qPCR analysis showed that Programin did not activate Oct4, Sox2, KLF4, c-Myc and, Nanog expression in the cells cultured as a monolayer.

HUCPV cells that were aggregated into embryoid-like bodies showed higher expression of Oct4, Sox2 and Nanog compared to those cells cultured as a monolayer (FIG. 6). However, Klf4 and c-Myc expression were not activated.

Figure 7:
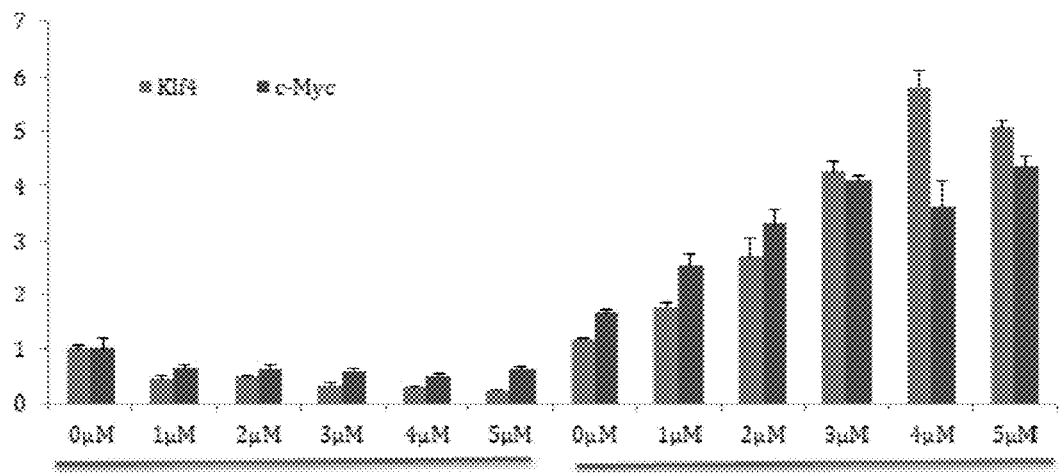
FIG. 7 provides a higher resolution of the qPCR data in FIG. 6.
Figure 8A:
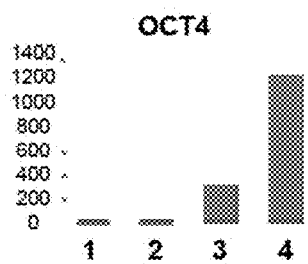
FIGS. 8A-8E provides qPCR results showing the level of Oct4 (FIG. 8A), Nanog (FIG. 8B), Sox2 (FIG. 8C), c-Myc (FIG. 8D) and KLF4 (FIG. 8E) in human skin fibroblast grown in a monolayer or grown as an aggregate (e.g., embryoid-like body), and treated with 5 µM programin for 4 days.
Figure 8B:
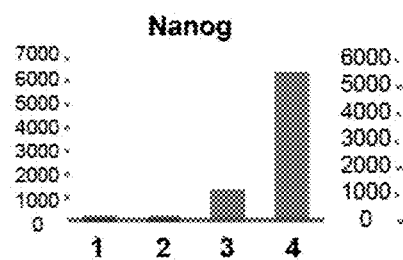
Figure 8C:
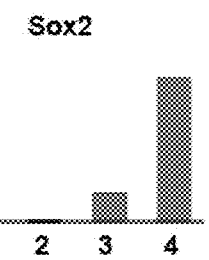
Figure 8D:
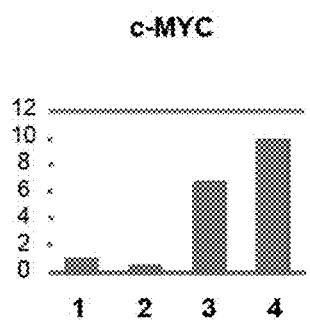
Figure 8E:
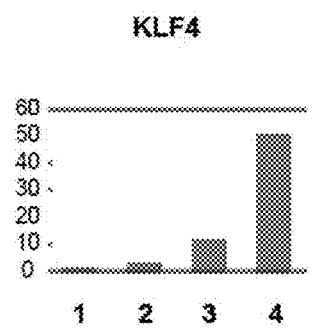

The embryoid-like bodies formed from HUCPV cells were treated with 1-5 µM Programin for 30 hours. Embryoid-like bodies exposed to Programin at all concentrated tested showed significantly enhanced Oct4, Sox2, KLF4, c-Myc and, Nanog expression compared to the untreated embryoid-like body controls (0 µM) (FIGS. 6 and 7). 4 µM Programin induced the highest level of Oct4, Sox2, Klf4 and Nanog compared to the other concentrations.

The data illustrates that HUCPV cells when physically aggregated into embryoid-like bodies respond to Programin by activating Oct4, Sox2, Klf4, c-Myc and, Nanog expression in the cells. The embryoid-like bodies formed originally from HUCPV cells differentiate into pluripotent stem cells when grown on non-adhesive culture dishes and prevented from sticking to the dish surface.

Example 3: Protocol for Activating Pluripotent Gene Expression in Human Skin Fibroblasts This example illustrates a method of inducing the formation of iPSCs from human skin fibroblasts. The method includes forming the human fibroblasts into cell aggregates and then exposing the aggregates to the compound programin or a derivative thereof, e.g., programin 2-9.

Materials required: Fibroblast medium, supplemented with 15% FBS, 1% non-essential amino acids, 1% PS in Eagle's MEM medium (Invitrogen), human ESC medium, supplemented with 20% knockout serum replacement (Invitrogen), 2 mM L-glutamine, 0.1 mM non-essential amino acids, 0.1 mM mercaptoethanol, 10 ng/mL fibroblast growth factor-basic (bFGF), 1% PS in DMEM/F12 (Invitrogen), Programin or derivatives thereof (frozen stock dissolved in DMSO); Working concentration=5 µM, and sterile 35 mm non-adhesive culture dish (SPL; 11035).

Procedure:
1. Primary human skin fibroblasts were cultured in fibroblast medium and passaged by trypsinization. Passage 5 fibroblasts were used for experimentation.
2. After dissociating the cultures into single cells with trypsin, $2\times10^6$ cells were resuspended in 3 mL fibroblast medium in non-adhesive 35 mm dish and maintained in 37° C. incubator with 5% $CO_2$.
3. Several hours later, aggregates were formed. Gently breakup excessively large aggregates by pipetting.
4. The next day, compact aggregates were formed. Again gentry breakup aggregates into smaller size (100-120 µm diameter) by pipetting.
5. Three days after cell aggregate/embryoid-like cell body formation, change the medium to human ESC medium supplemented with 5 µM Programin or derivatives thereof.
6. Replenish medium with fresh Programin or derivatives thereof 2 days after.
7. Harvest cells after 4 days of treatment with Programin or derivatives thereof. Extract total RNA using Trizol Reagent and purify using column.
8. Perform reverse-transcription and qPCR for key stem cells-associate genes.

Results:
After 4 days of compound treatment, stem cell-associated genes such as Oct4, Nanog, Sox2, c-Myc and KLF4 are expressed at higher levels in the embryoid-like bodies treated with programin than embryoid-like bodies treated with vehicle, a monolayer of human skin fibroblasts treated with programin, and a monolayer of human skin fibroblasts treated with vehicle (FIGS. 8A-E). Thus, Programin activates fibroblasts cultured in an aggregate, but not in a monolayer, to strongly express pluripotency-associated genes including: Oct4, Sox2, Nanog, KLF4 and c-Myc.

Example 4: Method for Testing the Developmental Potential of the Embryoid-Like Bodies Generated According to the Examples Above This example illustrates methods of differentiating the iPSCs produced according to the methods described in Examples 1-3 to osteogenic cells or neural cells.

Method for Osteogenic (Bone) Induction:

Programin-treated embryoid-like cell bodies ($1 \times 10^6$ cells/10 cm$^2$) were maintained as a suspension culture in DMEM/F12, 1000 U/mL LIF and 1×B27 on non-adhesive culture dishes for 4 days. The embryoid-like cell bodies were then transferred to culture dishes coated with 0.1% gelatin (FIG. 9A). 10 μM Wnt agonist (Cat#681665, Calbiochem) was added to the culture medium (DMEM/F12, 1000 U/mL LIF and 1×B27). Bone-like nodules were evident in the cultures after 2-3 days (FIG. 9B). Alizen Red s staining of the nodules confirmed that the differentiated cells were osteocytes (FIG. 9C). Programin-treated cells that were not aggregated underwent cell death following exposure to the Wnt agonist (FIG. 9D).

Method for Nerve Cell Induction:

Programin treated embryoid-like cell bodies ($1 \times 10^6$ cells/10 cm$^2$) were maintained as a suspension culture in DMEM/F12, 1000 U/mL LIF and 1×B27 on non-adhesive culture dishes for 4 days. The embryoid-like cell bodies were then transferred to culture dishes coated with 0.1% gelatin (FIG. 10A). No nerve-inducing small molecules were added to the media because the B27 in the culture medium can induce neurogenesis (FIG. 10B). Neurons were evident on the 0.1% gelatin coated culture plates after 3 days culture, and more obvious after 7 days (FIGS. 10C and D).

All patents, patent applications, and other publications, including GenBank Accession Numbers, cited in this application are incorporated by reference in the entirety for all purposes.

What is claimed is:

1. A method for increasing Oct4, Sox2, or Nanog expression in fibroblasts, the method comprising:
   (a) culturing the fibroblasts in a vessel;
   (b) mechanically agitating the fibroblasts that are unattached to the vessel to form a non-adherent cellular aggregate; and
   (c) exposing the non-adherent cellular aggregate to an effective amount of a compound of Formula II-IX having any one of the following structures:

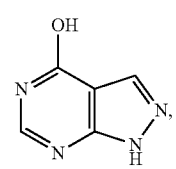

(II)

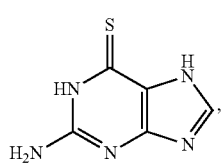

(III)

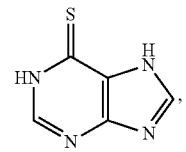

(IV)

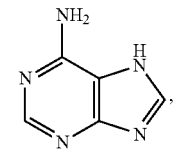

(V)

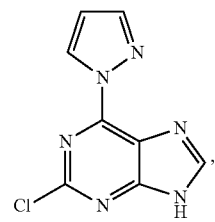 [SMILES: Clc1nc(-n2cccn2)c2nc[nH]c2n1]

(VI)

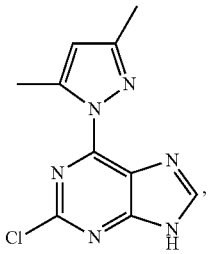

(VII)

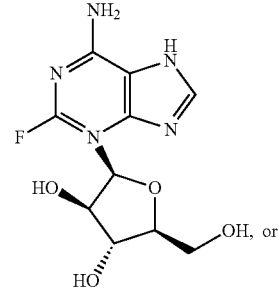

(VIII)

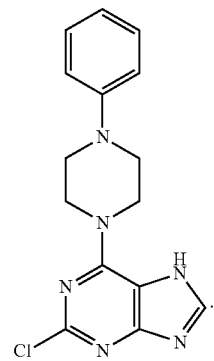

(IX)

thereby increasing Oct4, Sox2, or Nanog expression in the fibroblasts of the non-adherent cellular aggregate.

2. The method of claim 1, further comprising step (d) detecting the expression level of Oct4, Sox2, or Nanog in the fibroblasts of the non-adherent cellular aggregate.

3. The method of claim 2, further comprising step (e) isolating the fibroblasts of the non-adherent cellular aggregate.

4. The method of claim 1, wherein the fibroblasts are human fibroblasts.

5. The method of claim 1, wherein the fibroblasts are murine fibroblasts.

6. The method of claim 1, wherein the fibroblasts of step (a) are at a density of about $1\times10^5$-$1\times10^6$ cells/cm$^2$.

7. The method of claim 1, wherein mechanically agitating comprises titurating, stirring or rocking the fibroblasts.

8. The method of claim 2, wherein step (d) comprises an amplification-based assay, a hybridization-based assay, an immunoassay or a flow cytometry assay.

9. The method of claim 2, wherein the expression level of Oct4, Sox2 or Nanog in the fibroblasts of the non-adherent cellular aggregate is at least about 20-fold to about 200-fold higher compared to the expression level in the fibroblasts prior to step (b).

10. The method of claim 3, further comprising, subsequent to step (e), expanding the isolated fibroblasts.

* * * * *